US012559567B2

(12) United States Patent
Perkins et al.

(10) Patent No.: US 12,559,567 B2
(45) Date of Patent: Feb. 24, 2026

(54) METHODS FOR CREATING SYNTHETIC CHROMOSOMES HAVING GENE REGULATORY SYSTEMS AND USES THEREOF

(71) Applicant: SynPloid Biotek, LLC, Savannah, GA (US)

(72) Inventors: Edward Perkins, Savannah, GA (US); Amy Greene, Savannah, GA (US)

(73) Assignee: CarryGenes Bioengineering, LLC, Savannah, GA (US)

( * ) Notice: Subject to any disclaimer, the term of this patent is extended or adjusted under 35 U.S.C. 154(b) by 835 days.

(21) Appl. No.: 16/092,841

(22) PCT Filed: Apr. 12, 2017

(86) PCT No.: PCT/US2017/027270
§ 371 (c)(1),
(2) Date: Oct. 11, 2018

(87) PCT Pub. No.: WO2017/180786
PCT Pub. Date: Oct. 19, 2017

(65) Prior Publication Data
US 2019/0345259 A1 Nov. 14, 2019

Related U.S. Application Data

(60) Provisional application No. 62/321,720, filed on Apr. 12, 2016.

(51) Int. Cl.
*C07K 16/30* (2006.01)
*C07K 16/28* (2006.01)
(Continued)

(52) U.S. Cl.
CPC ...... *C07K 16/3007* (2013.01); *C07K 16/2803* (2013.01); *C07K 16/32* (2013.01);
(Continued)

(58) Field of Classification Search
CPC ............ C07K 16/3007; C07K 16/2803; C07K 16/32; C07K 2317/14; C07K 2317/622; C12N 15/85; C12N 2830/003
See application file for complete search history.

(56) References Cited

U.S. PATENT DOCUMENTS

| | | | |
|---|---|---|---|
| 2002/0160410 A1 | 10/2002 | Hadlaczky et al. | |
| 2004/0096891 A1 | 5/2004 | Bennett | |
(Continued)

FOREIGN PATENT DOCUMENTS

| | | |
|---|---|---|
| EP | 2218786 A4 | 6/2011 |
| EP | 2522725 B1 | 10/2016 |
(Continued)

OTHER PUBLICATIONS

Gao et al., 2020; Application of serine integrases for secondary metabolite pathway assembly in Streptomyces Synthetic and Systems Biotechnology pp. 111-119.*

(Continued)

*Primary Examiner* — Tracy Vivlemore
*Assistant Examiner* — Thomas R. Amick
(74) *Attorney, Agent, or Firm* — Susan Myers Fitch, Patent Agent

(57) ABSTRACT

The present invention encompasses compositions and methods to allow one to deliver and express multiple genes under the control of multiple gene regulatory components in a recipient cell via a synthetic chromosome. The engineering of synthetic chromosomes to contain multiple gene control units permits the construction of complex biological circuits.

13 Claims, 9 Drawing Sheets

ENGINEERING AND EXPRESSION OF MULTIPLE GENE CIRCUITS ON A SYNTHETIC CHROMOSOME. A) EXPRESSION OF GENE PRODUCTS 1 AND 2 WHEN BOTH INDUCERS ARE PRESENT. B) EXPRESSION OF PRODUCT 1 IS MADE IN THE PRESENCE OF INDUCER 1, IN THE ABSENCE OF INDUCER 1 AND THE PRESENCE OF INDUCER 2, ONLY PRODUCT 2 IS SYNTHESIZED FROM THE SYNTHETIC CHROMOSOME.

(51) Int. Cl.
  *C07K 16/32* (2006.01)
  *C12N 15/85* (2006.01)
(52) U.S. Cl.
  CPC .......... *C12N 15/85* (2013.01); *C07K 2317/14*
      (2013.01); *C07K 2317/622* (2013.01); *C12N*
      *2830/003* (2013.01)

(56) References Cited

U.S. PATENT DOCUMENTS

| | | | |
|---|---|---|---|
| 2004/0205834 A1* | 10/2004 | Massie | ............... C07K 14/4705 |
| | | | 435/325 |
| 2005/0181506 A1 | 8/2005 | Perkins et al. | |
| 2007/0004002 A1 | 1/2007 | Okazaki | |
| 2011/0318832 A1 | 12/2011 | Cech et al. | |
| 2012/0064578 A1 | 3/2012 | Perkins et al. | |
| 2012/0093785 A1 | 4/2012 | Oshimura et al. | |
| 2013/0202532 A1 | 8/2013 | Benenson et al. | |
| 2014/0295501 A1 | 10/2014 | Katona et al. | |
| 2015/0259684 A1 | 9/2015 | Church et al. | |
| 2018/0010150 A1 | 1/2018 | Perkins et al. | |

FOREIGN PATENT DOCUMENTS

| | | | |
|---|---|---|---|
| EP | 1559782 B1 | 12/2016 | |
| WO | 9740183 A2 | 10/1997 | |
| WO | 9942929 A1 | 8/1999 | |
| WO | 0018941 A1 | 4/2000 | |
| WO | 02096923 B1 | 5/2004 | |
| WO | 2015066722 A1 | 5/2015 | |

OTHER PUBLICATIONS

Broussau et al., Inducible Packaging Cells for Large-scale Production of Lentiviral Vectors in Serum-free Suspension Culture. www.moleculartherapy.org vol. 16 No. 3, 500-507 Mar. 2008.*
Brown et al Technology used to build and transfer mammalian chromosomes Experimental Cell Research vol. 388, Issue 2, Mar. 15, 2020. pp. 1-9.*
Merriam-Webster Definition autonomous downloaded Jan. 18, 2023 pp. 1-12.*
Miao et al Overexpression of CmWRKY8-1-VP64 Fusion Protein Reduces Resistance in Response to Fusarium oxysporum by Modulating the Salicylic Acid Signaling Pathway in Chrysanthemum morifolium, Int. J. Mol. Sci. 2023, pp. 1-16.*
Karn J, Stoltzfus CM. Transcriptional and posttranscriptional regulation of HIV-1 gene expression. Cold Spring Harb Perspect Med. Feb. 2012;2(2):a006916. doi: 10.1101/cshperspect.a006916. PMID: 22355797; PMCID: PMC3281586 (Year: 2012).*
Jung-Hyun Kim, et al., Comparative analysis and classification of highly divergent mouse rDNA units based on their intergenic spacer (IGS) variability, NAR Genomics and Bioinformatics, vol. 6, Issue 2, Jun. 2024 (Year: 2024).*
Kazuki, Yasuhiro, and Mitsuo Oshimura. "Human artificial chromosomes for gene delivery and the development of animal models." Molecular therapy : the journal of the American Society of Gene Therapy vol. 19,9 (2011): 1591-601. (Year: 2011).*
Lienert, Florian et al. "Synthetic biology in mammalian cells: next generation research tools and therapeutics." Nature reviews. Molecular cell biology vol. 15,2 (2014): 95-107. (Year: 2014).*
McStay, Brian. "Nucleolar organizer regions: genomic âdark matterârequiring illumination." Genes & development 30.14 (2016): 1598-1610.). That is, ribosomal DNA is apparently only found outside of the centromere, and is not considered to be centromeric DNA. (Year: 2016).*
Mehta, Gunjan D et al. âCentromere identity: a challenge to be faced.â Molecular genetics and genomics : MGG vol. 284,2 (2010): 75-94. doi:10.1007/s00438-010-0553-4 (Year: 2010).*
Weipoltshammer, Klara, et al. "Intranuclear anchoring of repetitive DNA sequences: centromeres, telomeres, and ribosomal DNA." The Journal of cell biology 147.7 (1999): 1409-1418. (Year: 1999).*

Extended European Search Report, issued Octoboer 14, 2019 in EP 17783084.1 based on PCT/US2017/027270.
Lindenbaum et al., "A mammalian artificial chromosome engineering system (ACE System) applicable to biopharmaceutical protein production, transgenesis and gene-based cell therapy," Nucleic Acids REsearch, (2004), vol. 32, No. 21, pp. e172 1-15.
Siuti et al., "Synthetic circuits integrating logic and memory in living cells," Nature Biotechnology, (2013), vol. 31, No. 5, pp. 448-452.
Teruhiko Suzuki et al., "A Novel System for Simultaneous or Sequential Integral of Multiple Gene-Loading Vectors into a Defined Site of a Human Artificial Chromosome," PLOS ONE, vol. 9, No. 10, pp. 1-9.
Shigeyuki Yamaguchi et al., "A Method for Producing Transgenic Cells Using a Multi-Integrase System on a Human Artificial Chromosome Vector," PLOS One, Public Library of Science, US, vol. 6, No. 2, p. e17267-1.
Martella, et al., "Mammalian Synthetic Biology: Time for Big MACS," ACS Synthetic Biology, vol. 5, No. 10, pp. 1040-1049.
Basu, J., "Artificial and Engineered Chromosomes: Non-Integrating Vectors for Gene Therapy." Trends in Molecular Medicine, Elsevier Current Trends, vol. 11 (5), pp. 251-258 (2005).
Ikeno, M et al., "Construction of YAC-based mammalian artificial chromosomes", Nature Biotechnology, (19980500), vol. 16, No. 5, pp. 431-439, XP009060040.
International Search Report issued Sep. 29, 2017 in PCT/US17/27270.
Katoh, et al., (2004) "Construction of a novel human artificial chromosome vector for gene delivery." Biochem. Biophys. Res. Comm. 321:280-290.
Kazuki, et al., "Refined human artificial chromosome vectors for gene therapy and animal transgenesis." Gene Therapy, vol. 18(4):384-393 (2010).
Kazuki, Y et al., "Human Artificial Chromosomes for Gene Delivery and the Development of Animal Models", Molecular Therapy, (2011) 19(9):1591-1601. doi:10.1038/mt.2011.136, XP055581607.
Kouprina et al., (2013) "A new generation of human artificial chromosomes for functional genomics and gene therapy", Cell Mol Life Sci., vol. 70, No. 7, pp. 1135-1148, XP055470579.
Kouprina, et al., (2014) "Human Artificial Chromosome-Based Gene Delivery Vectors for Biomedicine and Biotechnology." Expert Opinion on Drug Delivery. 11(4):517-535.
Kurosaki, et al., "Integration-free and stable expression of FVIII using a human artificial chromosome." Journal of Human Genetics, vol. 56 (10), pp. 727-733 (2011).
Ren, X et al., "A Novel Human Artificial Chromosome Vector Provides Effective Cell Lineage-Specific Transgene Expression in Human Mesenchymal Stem Cells", Stem Cells, (Nov. 1, 2005), vol. 23, No. 10, doi:10.1634/stemcells.2005-0021, pp. 1608-1616, XP055473399.
Rocchi, et al., (2010) "Escherichia coli-Cloned CTFR Loci Relevant for Human Artificial Chromosome Therapy." Human Gene Therapy, 21:1077-1092.
Shitara, et al., 2008, "Telomerase-mediated life-span extension of human primary fibroblasts by human artificial chromosome (HAC) vector." Biochem. Biophys. Res. Commun. 369(3):807-11.
Takiguchi, et al., "A Novel and Stable Mouse Artificial Chromosome Vector." ACS Synthetic Biology, vol. 3 (12), pp. 903-914 (2014).
Toth, et al., "Novel Method to Load Multiple Genes onto a Mammalian Artificial Chromosome." Plos One, Public Library of Science, US, vol. 9 (1), pp. e85565-e85571 (2014).
Vanderbyl, S et al., "Transfer and Stable Transgene Expression of a Mammalian Artificial Chromosome into Bone Marrow-Derived Human Mesenchymal Stem Cells", Stem Cells, (20040500), vol. 22, No. 3, doi:doi:10.1634/stemcells.22-3-324, pp. 324-333, XP002506658.
Brenda Grimes and Zoia Monaco, "Artificial and Engineered Chromosomes: Developments and Prospects for Gene Therapy," Chromosoma, (2005), 114:230-241.
Bruce Bunnell, et al., "Development of Mammalian Artificial Chromosomes for the Treatment of Genetic Diseases: Sandhoff and Krabbe Diseases," Expert Opin. Biol. Therapy (2005) 5(2):95-206.

(56)             References Cited

OTHER PUBLICATIONS

Tomohiro Tsuduki, et al., "An Artificially Constructed De Novo Human Chromosome Behaves Almost Identically to Its Natural Counterpart during Metaphase and Anaphase in Living Cells," Molecular and Cellular Biology (2006), vol. 26, No. 20, p. 7682-7695.
Yueju Wang, et al., "Recombinase Technology: Applications and Possibilities," Plant Cell Rep., (2011), 30:267-285.

* cited by examiner

ENGINEERING AND EXPRESSION OF MULTIPLE GENE CIRCUITS ON A SYNTHETIC CHROMOSOME. A) EXPRESSION OF GENE PRODUCTS 1 AND 2 WHEN BOTH INDUCERS ARE PRESENT. B) EXPRESSION OF PRODUCT 1 IS MADE IN THE PRESENCE OF INDUCER 1. IN THE ABSENCE OF INDUCER 1 AND THE PRESENCE OF INDUCER 2, ONLY PRODUCT 2 IS SYNTHESIZED FROM THE SYNTHETIC CHROMOSOME.

Gene Inducer 1
Gene Inducer 2
Gene Product 1
Gene Product 2
Gene 1 on SynC
Gene 2 on SynC AMPLIFICATION OF SYNTHETIC CIRCUIT
SIGNAL OUTPUT. NO PRODUCTION OF
GENE PRODUCTS 1 AND 2 WHEN
INDUCER 1 IS ABSENT. WHEN INDUCER
1 IS PRESENT, GENE PRODUCT 1 IS
PRODUCED AND POSITIVELY REGULATES
THE EXPRESSION OF GENE 2 AND LEADS
TO THE SYNTHESIS OF GENE PRODUCT 2.

ADDITION OF INDUCER 1

INHIBITION OF SYNTHETIC BIOLOGICAL CIRCUIT. IN THE ABSENCE OF INDUCER 1 AND THE PRESENCE OF INDUCER 2, GENE PRODUCT 2 IS MADE. WHEN INDUCER 1 IS ADDED, GENE PRODUCT 1 IS SYNTHESIZE LEADING TO THE NEGATIVE REGULATION AND HALTING OF GENE PRODUCT 2 PRODUCTION EVEN IN THE PRESENCE OF INDUCER 2

Gene Inducer 1

Gene Inducer 2

Gene Product 1

Gene Product 2

Gene Product 3

Gene 1 on SynC

Gene 2 on SynC

Gene 3 on SynC

THE LOGICAL AND CIRCUIT. ONLY
IN THE PRESENCE OF INDUCER 1
AND 2 ARE GENE PRODUCTS 1 AND
2 PRODUCED LEADING TO THE
PRODUCTION OF GENE PRODUCT 3

THE LOGICAL OR CIRCUIT. IN THE PRESENCE OF EITHER INDUCER 1 OR 2, GENE PRODUCTS 1 OR 2 ARE PRODUCED LEADING TO THE PRODUCTION OF GENE PRODUCT 3

METHODS FOR CREATING SYNTHETIC CHROMOSOMES HAVING GENE REGULATORY SYSTEMS AND USES THEREOF

CROSS REFERENCE TO RELATED APPLICATIONS

The present application is a USC § 371 National Stage filing entitled to the benefit of the filing date of International PCT Patent Application No. PCT/US17/27270 filed Apr. 12, 2017; which itself is entitled to the benefit of the filing date under 35 USC § 119(e). U.S. Provisional Patent Application No. 62/321,720, filed Apr. 12, 2016. The contents of each of these Patents and Patent Applications are incorporated herein in their entireties by reference thereto.

STATEMENT REGARDING GOVERNMENT SUPPORT

This invention was made with the support of the United States Government under contract D15PC00008 awarded by DARPA. The U.S. Government has certain rights in this invention.

FIELD OF THE INVENTION

The field of the invention encompasses methods to allow one to engineer synthetic chromosomes to deliver multiple genes under the control of multiple gene regulatory components.

BACKGROUND OF THE INVENTION

In the following discussion certain articles and methods will be described for background and introductory purposes. Nothing contained herein is to be construed as an "admission" of prior art. Applicant expressly reserves the right to demonstrate, where appropriate, that the articles and methods referenced herein do not constitute prior art under the applicable statutory provisions.

A number of gene regulation control systems have been developed for the controlled expression of genes in cells, both plant and animal. These systems include the tetracycline-controlled transcriptional activation system (Tet-On/ Tet-Off, Clontech, Inc. (Palo Alto, CA); Bujard and Gossen, PNAS, 89 (12):5547-5551 (1992)), the Lac Switch Inducible system (Wyborski et al., Environ Mol Mutagen, 28 (4):447-58 (1996); DuCoeur et al., Strategies 5 (3):70-72 (1992); U.S. Pat. No. 4,833,080), the ecdysone-inducible gene expression system (No et al., PNAS, 93 (8):3346-3351 (1996)), the cumate gene-switch system (Mullick et al., BMC Biotechnology, 6:43 (2006)), and the tamoxifen-inducible gene expression (Zhang et al., Nucleic Acids Research, 24:543-548 (1996)) as well as others. The goal of these control systems is for the regulatable production of proteins for both in vitro and in vivo experiments. However, the individual application of these systems is essentially "one-off", that is, a single gene under a single control system does not allow construction of complex biological circuits with a variety of logical control mechanisms.

The ability to generate fully-functional mammalian synthetic chromosomes represents a powerful system for cell-based correction of genetic disorders and production of biological pathways. Fully-functional mammalian synthetic chromosomes offer several advantages over bacterial-based and viral-based delivery systems including increased payload size, the fact that extrachromosomal maintenance avoids potential host-cell disruption, avoidance of transcriptional silencing of introduced genes and possible immunological complications, and mammalian synthetic chromosomes can be derived from and tailored to the species into which the synthetic chromosome is to be inserted. Because synthetic chromosomes can be engineered to contain multiple site-specific integration sites and can carry a big payload, synthetic chromosomes provide an opportunity to build portable biological circuit boards on which can be loaded multiple gene control systems. There is a need in the art for the ability to construct complex biological expression control systems. The present invention provides methods and compositions that address this need.

SUMMARY OF THE INVENTION

This Summary is provided to introduce a selection of concepts in a simplified form that are further described below in the Detailed Description. This Summary is not intended to identify key or essential features of the claimed subject matter, nor is it intended to be used to limit the scope of the claimed subject matter. Other features, details, utilities, and advantages of the claimed subject matter will be apparent from the following written Detailed Description, including those aspects illustrated in the accompanying drawings and defined in the appended claims.

In some embodiments, the present invention provides a method for engineering a recipient cell with at least two target nucleic acids each under control of a regulatory control system, comprising: transfecting a first recipient cell line with synthetic chromosome production components including nucleic acid sequences that allow for site-specific integration of target nucleic acid sequences; producing a synthetic platform chromosome with multiple site-specific recombination sites; transfecting the first recipient cell line with a first delivery vector comprising a first target nucleic acid under control of a first regulatory control system; activating site-specific recombination between the synthetic platform chromosome and the first delivery vector, wherein the first target nucleic acid under control of the first regulatory control system is loaded onto the synthetic platform chromosome to produce a synthetic chromosome expressing the first target nucleic acid under control of the first regulatory control system; isolating a second recipient cell comprising the synthetic chromosome expressing the first target nucleic acid under control of the first regulatory control system; growing the second recipient cells; transfecting the second recipient cells with a second delivery vector comprising a second target nucleic acid under control of a second regulatory control system; activating site-specific recombination between the synthetic platform chromosome and the second delivery vector, wherein the second target nucleic acid under control of the second regulatory control system is loaded onto the synthetic platform chromosome to produce a synthetic chromosome expressing the first target nucleic acid under control of the first regulatory control system and the second target nucleic acid under control of the second regulatory control system; and isolating a third recipient cell comprising the synthetic chromosome expressing the first target nucleic acid under control of the first regulatory control system and the second target nucleic acid under control of the second regulatory control system.

In some aspects of this embodiment, the method further comprises the step of inducing transcription of the first and second target nucleic acids via the first and second regulatory control systems.

Yet other embodiments of the present invention provide a method for engineering a recipient cell with at least two target nucleic acids each under control of a regulatory control system, comprising: transfecting a first recipient cell line with synthetic chromosome production components including nucleic acid sequences that allow for site-specific integration of target nucleic acid sequences; producing a synthetic platform chromosome with multiple site-specific recombination sites; transfecting the first recipient cell line with a first delivery vector comprising a first target nucleic acid under control of a first regulatory control system, wherein a gene product of the first target nucleic acid regulates transcription of a second target nucleic acid; activating site-specific recombination between the synthetic platform chromosome and the first delivery vector, wherein the first target nucleic acid under control of the first regulatory control system is loaded onto the synthetic platform chromosome to produce a synthetic chromosome expressing the first target nucleic acid under control of the first regulatory control system; isolating a second recipient cell comprising the synthetic chromosome expressing the first target nucleic acid under control of the first regulatory control system; growing the second recipient cells; transfecting the second recipient cells with a second delivery vector comprising a second target nucleic acid under control of a second regulatory control system, wherein the second regulatory control system is regulated by the gene product of the first target nucleic acid; activating site-specific recombination between the synthetic platform chromosome and the second delivery vector, wherein the second target nucleic acid under control of the second regulatory control system is loaded onto the synthetic platform chromosome to produce a synthetic chromosome expressing the first target nucleic acid under control of the first regulatory control system and the second target nucleic acid under control of the second regulatory control system; isolating a third recipient cell comprising the synthetic chromosome expressing the first target nucleic acid under control of the first regulatory control system and the second target nucleic acid under control of the second regulatory control system; inducing transcription of the first target nucleic acid via the first regulatory control system to produce the first gene product; and regulating transcription of the second target nucleic acid via the first gene product.

In some aspects of this embodiment, the gene product of the first target nucleic acid induces transcription of the second target nucleic acid; and in some embodiments, the gene product of the first target nucleic acid suppresses transcription of the second target nucleic acid.

Yet other embodiments of the present invention provide a method for engineering a recipient cell with at least three target nucleic acids each under control of a regulatory control system, comprising: transfecting a first recipient cell line with synthetic chromosome production components including nucleic acid sequences that allow for site-specific integration of target nucleic acid sequences; producing a synthetic platform chromosome with multiple site-specific recombination sites; transfecting the first recipient cell line with a first delivery vector comprising a first target nucleic acid under control of a first regulatory control system, wherein a gene product of the first target nucleic acid regulates transcription of a third target nucleic acid; activating site-specific recombination between the synthetic platform chromosome and the first delivery vector, wherein the first target nucleic acid under control of the first regulatory control system is loaded onto the synthetic platform chromosome to produce a synthetic chromosome expressing the first target nucleic acid under control of the first regulatory control system isolating a second recipient cell comprising the synthetic chromosome expressing the first target nucleic acid under control of the first regulatory control system; growing the second recipient cells; transfecting the second recipient cells with a second delivery vector comprising a second target nucleic acid under control of a second regulatory control system, wherein a gene product of the second target nucleic acid regulates transcription of a third target nucleic acid; activating site-specific recombination between the synthetic platform chromosome and the second delivery vector, wherein the second target nucleic acid under control of the second regulatory control system is loaded onto the synthetic platform chromosome to produce a synthetic chromosome expressing the first target nucleic acid under control of the first regulatory control system and the second target nucleic acid under control of the second regulatory control system; isolating a third recipient cell comprising the synthetic chromosome expressing the first target nucleic acid under control of the first regulatory control system and the second target nucleic acid under control of the second regulatory control system; growing the third recipient cells; transfecting the third recipient cells with a third delivery vector comprising a third target nucleic acid under control of a third regulatory control system, wherein the gene products of the first and second target nucleic acids regulate transcription of the third target nucleic acid via the third regulatory control system; activating site-specific recombination between the synthetic platform chromosome and the third delivery vector, wherein the third target nucleic acid under control of the third regulatory control system is loaded onto the synthetic platform chromosome to produce a synthetic chromosome expressing the first target nucleic acid under control of the first regulatory control system, the second target nucleic acid under control of the second regulatory control system, and the third target nucleic acid under control of the third regulatory control system; inducing transcription of the first and second target nucleic acids via the first and second regulatory control systems to produce the first and second gene products; and regulating transcription of the third target nucleic acid via the first and second gene products.

In aspects of this embodiment, both the first and second gene products are necessary to regulate transcription of the third target nucleic acid; and in other embodiments, either the first or the second gene product regulates transcription of the third target nucleic acid. In some embodiments, regulation of the third target nucleic acid is inducing transcription of the third target nucleic acid, and in other embodiments, regulation of the third target nucleic acid is suppressing transcription of the third target nucleic acid.

In certain aspects of all the embodiments, the first and/or the second regulatory control systems may be selected from Tet-On, Tet-Off, Lac switch inducible, ecdysone-inducible, cumate gene-switch or tamoxifen-inducible system.

Additionally, aspects of all embodiments include the isolated cells comprising the synthetic chromosomes comprising the first; the first and second; and/or the first, second and third target nucleic acids; as well as the synthetic chromosomes upon which are loaded the first; the first and second; and the first, second and third target nucleic acids.

These and other aspects and uses of the invention will be described in the detailed description.

DETAILED DESCRIPTION OF THE INVENTION

Figure 1:
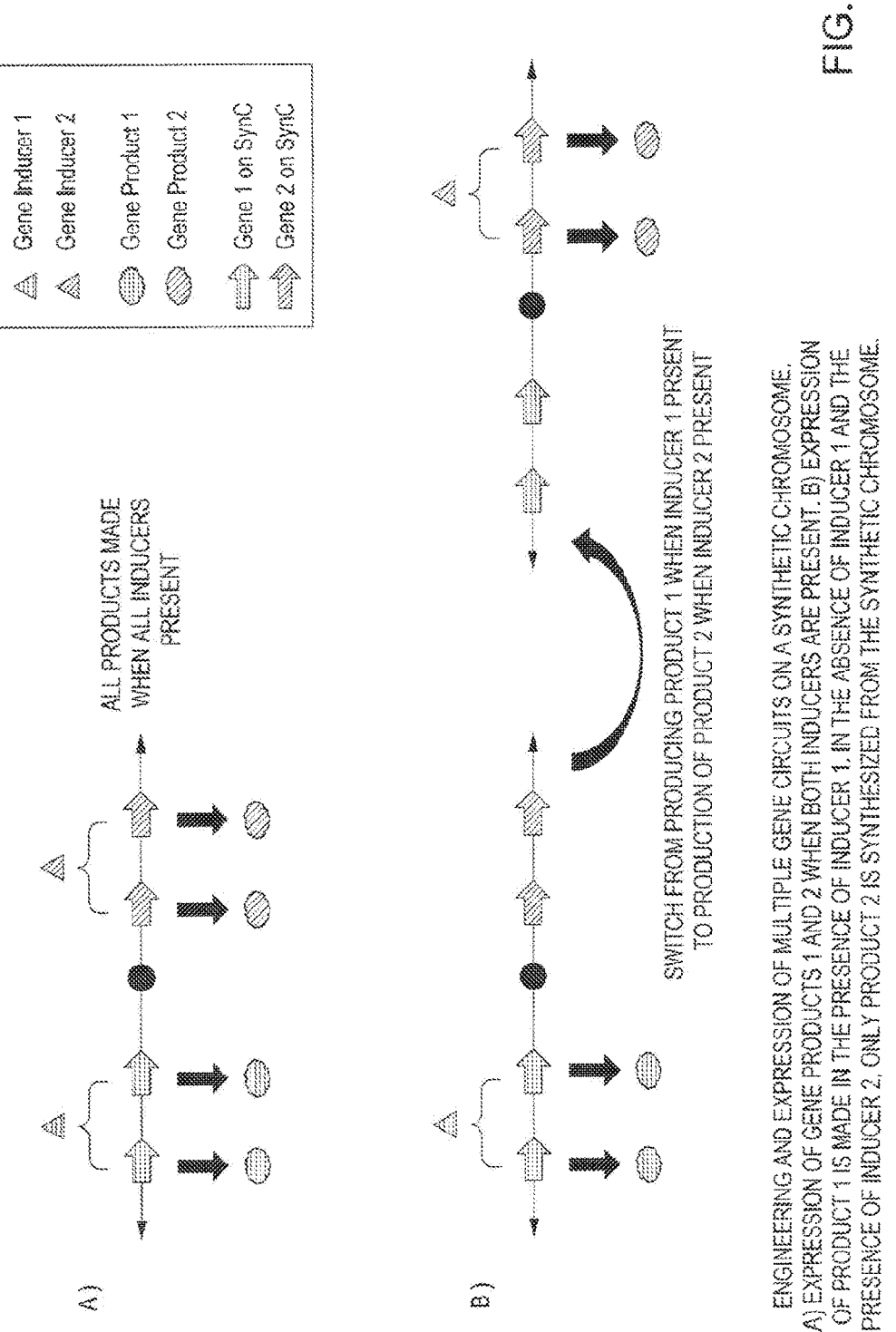
FIG. 1A is a simplified schematic of one embodiment of the methods of the present invention where gene 1 and gene 2 are under the control of different gene regulation control systems.
FIG. 1B is a simplified schematic of an embodiment of the methods of the present invention where there is a switch between gene products made when the inducer is changed.

The methods described herein may employ, unless otherwise indicated, conventional techniques and descriptions of molecular biology (including recombinant techniques), cell biology, biochemistry, and cellular engineering technology, all of which are within the skill of those who practice in the art. Such conventional techniques include oligonucleotide synthesis, hybridization and ligation of oligonucleotides, transformation and transduction of cells, engineering of recombination systems, creation of transgenic animals and plants, and human gene therapy. Specific illustrations of suitable techniques can be had by reference to the examples herein. However, equivalent conventional procedures can, of course, also be used. Such conventional techniques and descriptions can be found in standard laboratory manuals such as *Genome Analysis: A Laboratory Manual Series* (Vols. I-IV) (Green, et al., eds., 1999); *Genetic Variation: A Laboratory Manual* (Weiner, et al., eds., 2007); Sambrook and Russell, *Condensed Protocols from Molecular Cloning: A Laboratory Manual* (2006); and Sambrook and Russell, *Molecular Cloning: A Laboratory Manual* (2002) (all from Cold Spring Harbor Laboratory Press); *Protein Methods* (Bollag et al., John Wiley & Sons 1996); *Nonviral Vectors for Gene Therapy* (Wagner et al. eds., Academic Press 1999); *Viral Vectors* (Kaplift & Loewy, eds., Academic Press 1995); *Immunology Methods Manual* (Lefkovits ed., Academic Press 1997); *Gene Therapy Techniques, Applications and Regulations From Laboratory to Clinic* (Meager, ed., John Wiley & Sons 1999); M. Giacca, *Gene Therapy* (Springer 2010); *Gene Therapy Protocols* (LeDoux, ed., Springer 2008); *Cell and Tissue Culture: Laboratory Procedures in Biotechnology* (Doyle & Griffiths, eds., John Wiley & Sons 1998); *Mammalian Chromosome Engineering—Methods and Protocols* (G. Hadlaczky, ed., Humana Press 2011); *Essential Stem Cell Methods*, (Lanza and Klimanskaya, eds., Academic Press 2011); *Stem Cell Therapies: Opportunities for Ensuring the Quality and Safety of Clinical Offerings: Summary of a Joint Workshop* (Board on Health Sciences Policy, National Academies Press 2014); *Essentials of Stem Cell Biology*, Third Ed., (Lanza and Atala, eds., Academic Press 2013); and *Handbook of Stem Cells*, (Atala and Lanza, eds., Academic Press 2012), all of which are herein incorporated by reference in their entirety for all purposes. Before the present compositions, research tools and methods are described, it is to be understood that this invention is not limited to the specific methods, compositions, targets and uses described, as such may, of course, vary. It is also to be understood that the terminology used herein is for the purpose of describing particular aspects only and is not intended to limit the scope of the present invention, which will be limited only by the appended claims.

Note that as used in the present specification and in the appended claims, the singular forms "a," "and," and "the" include plural referents unless the context clearly dictates otherwise. Thus, for example, reference to "a composition" refers to one or mixtures of compositions, and reference to "an assay" includes reference to equivalent steps and methods known to those skilled in the art, and so forth.

Unless defined otherwise, all technical and scientific terms used herein have the same meaning as commonly understood by one of ordinary skill in the art to which this invention belongs. All publications mentioned herein are incorporated herein by reference for the purpose of describing and disclosing devices, formulations and methodologies which are described in the publication and which might be used in connection with the presently described invention.

Where a range of values is provided, it is understood that each intervening value between the upper and lower limit of that range and any other stated or intervening value in that stated range is encompassed within the invention. The upper and lower limits of these smaller ranges may independently be included in the smaller ranges, subject to any specifically excluded limit in the stated range. Where the stated range includes both of the limits, ranges excluding only one of those included limits are also included in the invention.

In the following description, numerous specific details are set forth to provide a more thorough understanding of the present invention. However, it will be apparent to one of ordinary skill in the art upon reading the specification that the present invention may be practiced without one or more of these specific details. In other instances, well-known features and procedures well known to those skilled in the art have not been described in order to avoid obscuring the invention.

Definitions

Unless expressly stated, the terms used herein are intended to have the plain and ordinary meaning as understood by those of ordinary skill in the art. The following definitions are intended to aid the reader in understanding the present invention, but are not intended to vary or otherwise limit the meaning of such terms unless specifically indicated.

"Binding" as used herein with reference to an nucleic acid-binding domain of a polypeptide) refers to a non-covalent interaction between a polypeptide and a nucleic acid. While in a state of non-covalent interaction, the polypeptide and nucleic acid are said to be "associated", "interacting", or "binding". Binding interactions are generally characterized by a dissociation constant (Kd) of less than $10^{-6}$ M to less than $10^{-15}$ M. "Affinity" refers to the strength of binding, increased binding affinity being correlated with a lower Kd.

By 'binding domain' it is meant a polypeptide or protein domain that is able to bind non-covalently to another molecule. A binding domain can bind to, for example, a DNA molecule (a DNA-binding protein), an RNA molecule (an RNA-binding protein) and/or a protein molecule (a protein-binding protein).

A "centromere" is any nucleic acid sequence that confers an ability of a chromosome to segregate to daughter cells through cell division. A centromere may confer stable segregation of a nucleic acid sequence, including a synthetic chromosome containing the centromere, through mitotic and meiotic divisions. A centromere does not necessarily need to be derived from the same species as the cells into which it is introduced, but preferably the centromere has the ability to promote DNA segregation in cells of that species. A "dicentric" chromosome is a chromosome that contains two centromeres. A "formerly dicentric chromosome" is a chromosome that is produced when a dicentric chromosome fragments. A "chromosome" is a nucleic acid molecule—and associated proteins—that is capable of replication and segregation in a cell upon division of the cell. Typically, chromosome contains a centromeric region, replication origins, telomeric regions and a region of nucleic acid between the centromeric and telomeric regions. An "acrocentric chromosome" refers to a chromosome with arms of unequal length.

A "coding sequence" or a sequence that "encodes" a peptide is a nucleic acid molecule that is transcribed (in the case of DNA) and translated (in the case of mRNA) into a polypeptide in vivo when placed under the control of appropriate control sequences. The boundaries of the coding sequence typically are determined by a start codon at the 5' (amino) terminus and a translation stop codon at the 3' (carboxy) terminus.

The term DNA "control sequences" refers collectively to promoter sequences, polyadenylation signals, transcription termination sequences, upstream regulatory domains, origins of replication, internal ribosome entry sites, enhancers, and the like, which collectively provide for the replication, transcription and translation of a coding sequence in a recipient cell. Not all of these types of control sequences need to be present so long as a selected coding sequence is capable of being replicated, transcribed and translated in an appropriate host cell.

"Endogenous chromosomes" refer to chromosomes found in a cell prior to generation or introduction of a synthetic chromosome.

As used herein, "euchromatin" refers to chromatin that stains diffusely and that typically contains genes, a ad "heterochromatin" refers to chromatin that remains unusually condensed and is thought to be transcriptionally inactive. Highly repetitive DNA sequences (satellite DNA) are usually located in regions of the heterochromatin surrounding the centromere.

The terms "heterologous DNA" or "foreign DNA" (or "heterologous RNA" or "foreign RNA") are used interchangeably and refer to DNA or RNA that does not occur naturally as part of the genome in which it is present, or is found in a location or locations and/or in amounts in a genome or cell that differ from that in which it occurs in nature. Examples of heterologous DNA include, but are not limited to, DNA that encodes a gene product or gene product(s) of interest. Other examples of heterologous DNA include, but are not limited to, DNA that encodes traceable marker proteins as well as regulatory DNA sequences.

The term "inducer" as used herein includes any biological molecule that directly or indirectly induces transcription of a gene, such as doxycycline in the Tet-On system, cumate in the Cumate-Switch system, other natural molecules as well as man-made, engineered molecules.

"Operably linked" refers to an arrangement of elements where the components so described are configured so as to perform their usual function. Thus, control sequences operably linked to a coding sequence are capable of effecting the expression of the coding sequence. The control sequences need not be contiguous with the coding sequence so long as they function to direct the expression of the coding sequence. Thus, for example, intervening untranslated yet transcribed sequences can be present between a promoter sequence and the coding sequence and the promoter sequence can still be considered "operably linked" to the coding sequence. In fact, such sequences need not reside on the same contiguous DNA molecule (i.e. chromosome), and may still have interactions resulting in altered regulation.

A "promoter" or "promoter sequence" is a DNA regulatory region capable of binding RNA polymerase in a cell and initiating transcription of a polynucleotide or polypeptide coding sequence such as messenger RNA, ribosomal RNAs, small nuclear or nucleolar RNAs or any kind of RNA transcribed by any class of any RNA polymerase I, II or III.

A "recipient cell" is a cell into which the components for creating a synthetic chromosome, a synthetic platform chromosome or a synthetic platform chromosome bioengineered to contain a given set of DNA elements. Types of recipient cell may include but are not limited to: stem cells, mesenchymal stem cells, adult derived stem cells, T-cells, immune cells, induced pluripotent stem cells, fibroblasts, endothelial cells, cells of the mesoderm, ectoderm and endoderm. Also included would be tumor cells cell culture lines, primary cells, and germ cells. The cells can then be, e.g., cultured, prepared for transplantation, used to create whole transgenic animals, and the like.

"Recognition sequences" are particular sequences of nucleotides that a protein, DNA, or RNA molecule, or combinations thereof (such as, but not limited to, a restriction endonuclease, a modification methylase or a recombinase) recognizes and binds. For example, a recognition sequence for Cre recombinase is a 34 base pair sequence containing two 13 base pair inverted repeats (serving as the recombinase binding sites) flanking an 8 base pair core and designated loxP (see, e.g., Sauer, Current Opinion in Biotechnology, 5:521-527 (1994)). Other examples of recognition sequences, include, but are not limited to, attB and attP, attR and attL and others that are recognized by the recombinase enzyme bacteriophage Lambda Integrase. The recombination site designated attB is an approximately 33 base pair sequence containing two 9 base pair core-type Int binding sites and a 7 base pair overlap region; attP is an approximately 240 base pair sequence containing core-type Int binding sites and arm-type Int binding sites as well as sites for auxiliary proteins IHF, FIS, and Xis (see, e.g., Landy, Current Opinion in Biotechnology, 3:699-7071 (1993)).

A "recombinase" is an enzyme that catalyzes the exchange of DNA segments at specific recombination sites. An integrase refers to a recombinase that is usually derived from viruses or transposons, as well as perhaps ancient viruses. "Recombination proteins" include excisive proteins, integrative proteins, co-factors and associated proteins that are involved in recombination reactions using one or more recombination sites (see, Landy, Current Opinion in Biotechnology, 3:699-707 (1993)). The recombination proteins used in the methods herein can be delivered to a cell via an expression cassette on an appropriate vector, such as a plasmid, and the like. In other embodiments, recombination proteins can be delivered to a cell in protein form in the same reaction mixture used to deliver the desired nucleic acid(s). In yet other embodiments, the recombinase could also be encoded in the cell and expressed upon demand using a tightly controlled inducible promoter.

"Ribosomal RNA" (rRNA) is the specialized RNA that forms part of the structure of a ribosome and participates in the synthesis of proteins. Ribosomal RNA is produced by transcription of genes which, in eukaryotic cells, are present in multiple copies. In human cells, the approximately 250 copies of rRNA genes (i.e., genes which encode rRNA) per haploid genome are spread out in clusters on at least five different chromosomes (chromosomes 13, 14, 15, 21 and 22). In human cells, multiple copies of the highly conserved rRNA genes are located in a tandemly arranged series of rDNA units, which are generally about 40-45 kb in length and contain a transcribed region and a nontranscribed region known as spacer (i.e., intergenic spacer) DNA which can vary in length and sequence.

As used herein the term "selectable marker" refers to a gene introduced into a cell, particularly in the context of this invention into cells in culture, that confers a trait suitable for artificial selection. General use selectable markers are well-known to those of ordinary skill in the art. In preferred embodiments, selectable markers for use in a human synthetic chromosome system should be non-immunogenic in the human and include, but are not limited to: human nerve growth factor receptor (detected with a MAb, such as described in U.S. Pat. No. 6,365,373); truncated human growth factor receptor (detected with MAb); mutant human dihydrofolate reductase (DHFR; fluorescent MTX substrate available); secreted alkaline phosphatase (SEAP; fluorescent substrate available); human thymidylate synthase (TS; confers resistance to anti-cancer agent fluorodeoxyuridine); human glutathione S-transferase alpha (GSTA1; conjugates glutathione to the stem cell selective alkylator busulfan; chemoprotective selectable marker in CD34$^+$ cells); CD24 cell surface antigen in hematopoietic stem cells; human CAD gene to confer resistance to N-phosphonacetyl-L-aspartate (PALA); human multi-drug resistance-1 (MDR-1; P-glycoprotein surface protein selectable by increased drug resistance or enriched by FACS); human CD25 (IL-2α, detectable by Mab-FITC); Methylguanine-DNA methyltransferase (MGMT; selectable by carmustine); and Cytidine deaminase (CD; selectable by Ara-C). Drug selectable markers such as puromycin, hygromycin, blasticidin, G418, tetracycline may also be employed. In addition, using FACs sorting, any fluorescent marker gene may be used for positive selection, as may chemiluminescent markers (e.g. Halotags), and the like.

"Site-specific recombination" refers to site-specific recombination that is effected between two specific sites on a single nucleic acid molecule or between two different molecules that requires the presence of an exogenous protein, such as an integrase or recombinase. Certain site-specific recombination systems can be used to specifically delete, invert, or insert DNA, with the precise event controlled by the orientation of the specific sites, the specific system and the presence of accessory proteins or factors. In addition, segments of DNA can be exchanged between chromosomes as described in FIG. 4 (chromosome arm exchange).

"Synthetic chromosomes" (also referred to as "artificial chromosomes") are nucleic acid molecules, typically DNA, that have the capacity to accommodate and express heterologous genes and that stably replicate and segregate alongside endogenous chromosomes in cells. A "mammalian synthetic chromosome" refers to chromosomes that have an active mammalian centromere(s). A "human synthetic chromosome" refers to a chromosome that includes a centromere that functions in human cells and that preferably is produced in human cells. For exemplary artificial chromosomes, see, e.g., U.S. Pat. Nos. 8,389,802; 7,521,240; 6,025,155; 6,077, 697; 5,891,691; 5,869,294; 5,721,118; 5,712,134; 5,695, 967; and 5,288,625 and published International PCT application Nos. WO 97/40183 and WO 98/08964.

The terms "subject", "individual" or "patient" may be used interchangeably herein and refer to a mammal, and in some embodiments, a human.

A "vector" is a replicon, such as plasmid, phage, viral construct, cosmid, bacterial artificial chromosome, P-1 derived artificial chromosome, or yeast artificial chromosome to which another DNA segment may be attached to some instances a vector may be a chromosome such as in the case of an arm exchange from one endogenous chromosome engineered to comprise a recombination site to a synthetic chromosome. Vectors are used to transduce and express a DNA segment in cell.

The Invention

The present invention encompasses compositions and methods to allow one to deliver and express multiple genes from multiple gene regulatory control systems all from a single synthetic chromosome. Synthetic chromosomes with their large carrying capacity can carry and express multiple gene products—and these multiple gene products can be under the control of different regulatory control systems—thereby circumventing the limitations of viral- and plasmid-based nucleic acid delivery. The present invention provides methods and compositions to allow for constructing a complex regulatable expression system on a synthetic platform chromosome, and is applicable to all methodologies of synthetic chromosome production, including the "top down" approach, the "bottom up" approach, engineering of naturally-occurring minichromosomes, and induced de novo chromosome generation by targeted amplification of specific chromosomal segments (all of which are discussed in more detail, infra).

Synthetic or ACE platform chromosomes are synthetic chromosomes that can be employed in a variety of cell-based protein production, modulation of gene expression or therapeutic applications. During the generation of synthetic platform chromosomes, unique DNA elements/sequences required for integrase mediated site-specific integration of heterologous nucleic acids are incorporated into the synthetic chromosome which allows for engineering of the synthetic chromosome. Since the integrase targeting sequences are amplified during synthetic chromosome production, a large number of site-specific recombination sites are incorporated onto the synthetic chromosome and are available for the multiple loading of the synthetic platform chromosome by delivery vectors containing multiple gene regulatory control systems.

An example of a synthetic platform chromosome with multiple gene regulatory control systems is a synthetic platform chromosome containing, both the Tet-On and Cumate Switch gene regulatory systems. The Tet-On and Cumate Switch regulatory control systems are engineered and expressed from the synthetic platform chromosome such that genes under the control of these regulatory control systems are expressed from a synthetic platform chromosome when an inducer is added; doxycycline is an inducer for the Tet-On system and cumate is an inducer for the Cumate Switch system. For example, therapeutic proteins such as antibodies or antibody fragments may be encoded on delivery vectors and loaded onto the synthetic chromosome platform such that the antibodies and/or fragments are under the control of the Tet-On or Cumate-Switch. All antibodies or antibody fragments are expressed simultaneously when the inducers doxycycline and cumate are both present. Alternatively, the Tet-On and Cumate-Switch—and the one or more genes under the control or the Tet-On or Cumate-Switch systems—can be induced independently. A schematic of this embodiment of the invention is shown in FIG. 1A. FIG. 1A shows the engineering and expression of two exemplary genes, gene 1 and gene 2, on a synthetic chromosome. When gene inducer 1 and gene inducer 2 are both present, both gene products 1 and 2 are expressed. When only gene inducer 1 is present, only gene product 1 is produced from the synthetic chromosome. When only gene inducer 2 is present, only gene product 2 is produced from the synthetic chromosome. FIG. 1B is a simplified schematic where expression of a gene product is made in the presence of inducer 1, and in the absence of inducer 1 and in the presence of inducer 2, only gene product 2 is synthesized from the synthetic chromosome.

Figure 2:
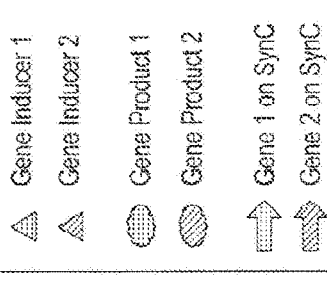
FIG. 2 is a simplified schematic of an alternative embodiment of the methods of the present invention where gene 1 is under the control of a gene regulation control system, and the expression of gene 2 is induced by the gene product of gene 1.
Figure 2:
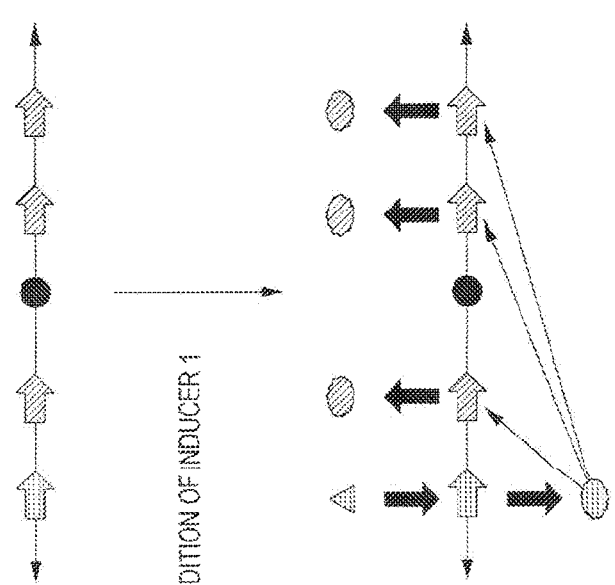

Another embodiment of using a synthetic chromosome for regulated gene expression is shown in FIG. 2. FIG. 2 illustrates a scenario where the gene product of a first expressed gene induces the expression of a second gene. FIG. 2 shows an exemplary biological circuit on a synthetic chromosome that provides amplification of signal output. There is no production of either gene product 1 or gene product 2 when inducer 1 is absent. However, when inducer 1 is present, gene 1 is transcribed, gene product 1 is expressed, and gene product 1 in turn induces the transcription and translation of gene 2 and the synthesis of gene product 2. One example of a use of this embodiment is the concerted expression of multiply-loaded genes that confer increased cell survival. In this exemplary scenario, multiply-loaded genes are positioned and expressed from a synthetic chromosome that confers increased immune cell survival in response to tumor challenge. Tumor cells employ a variety of means to escape recognition and reduce T-cell function; however, this challenge may be circumvented by engineering T-cells to express from a common regulatory control system multiply-loaded factors that inhibit cell cycle arrest response; e.g., expression of genes that code for inhibitors to the immune and cell cycle checkpoint proteins, such as anti-PD-1 (programmed cell death protein 1) and anti-CTLA-4 (central T-Cell activation and inhibition 4). Thus from one inducing regulatory control system, multiple gene products can be produced to enhance immune cell function.

Figure 3:
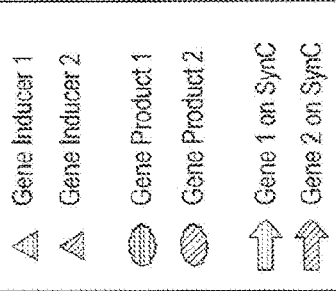
FIG. 3 is a simplified schematic of another alternative embodiment of the methods of the present invention, where gene 1 is under the control of a gene regulation control system, and the expression of gene 2 is suppressed by the gene product of gene 1.
Figure 3:
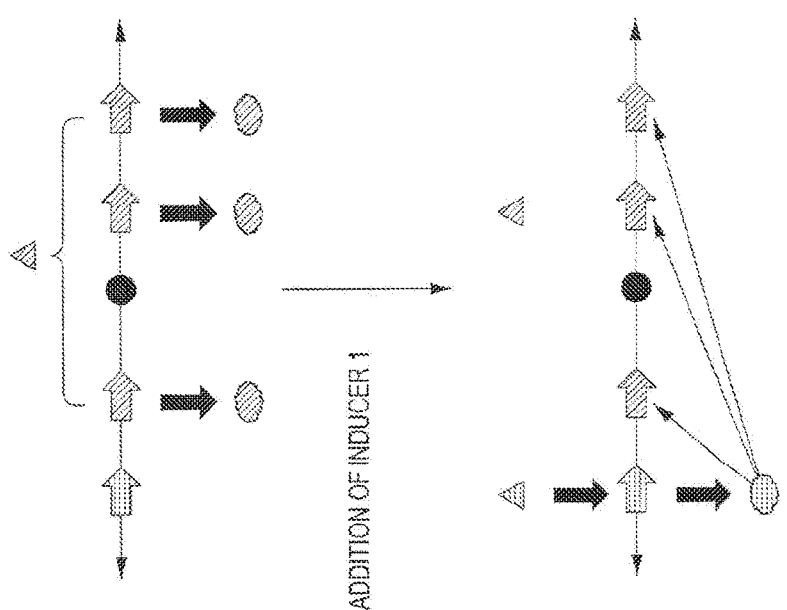

In contrast to the embodiment illustrated in FIG. 2, expression of a second gene from the synthetic chromosome, may be suppressed by the presence of a first gene product that is produced from a first gene under the control of a first regulatory control system. FIG. 3 shows inhibition of a biological circuit, where in the absence of inducer 1 and the presence of inducer 2, gene 2 is transcribed and gene product 2 is synthesized; however, in the presence of inducer 1 and inducer 2, inducer 1 suppresses the transcription of gene 2 and the synthesis of gene product 2.

Figure 4:
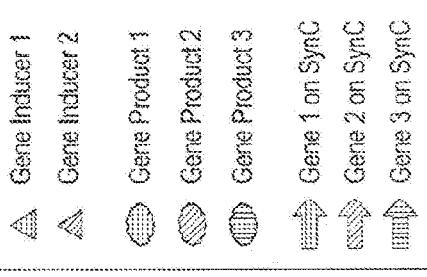
FIG. 4 is a simplified schematic of yet another embodiment of the methods of the present invention, where gene 1 and gene 2 are under the control of different gene regulation control systems, and gene 3 is induced by the combined gene products of genes 1 and 2.

In other embodiments of the present invention, more complex "logic" circuits are constructed. For example, a logical "AND" switch can be built such that the expression of two genes and the production of two gene products leads to the expression of a third gene and a production of a third product. FIG. 4 illustrates this embodiment. FIG. 4 shows that the presence of inducer 1 or inducer 2 by themselves is insufficient to induce the transcription of gene 3 and the synthesis of gene product 3; however, the combination of inducer 1 and inducer 2 induces the transcription of gene 3 and the synthesis of gene product 3.

Figure 5:
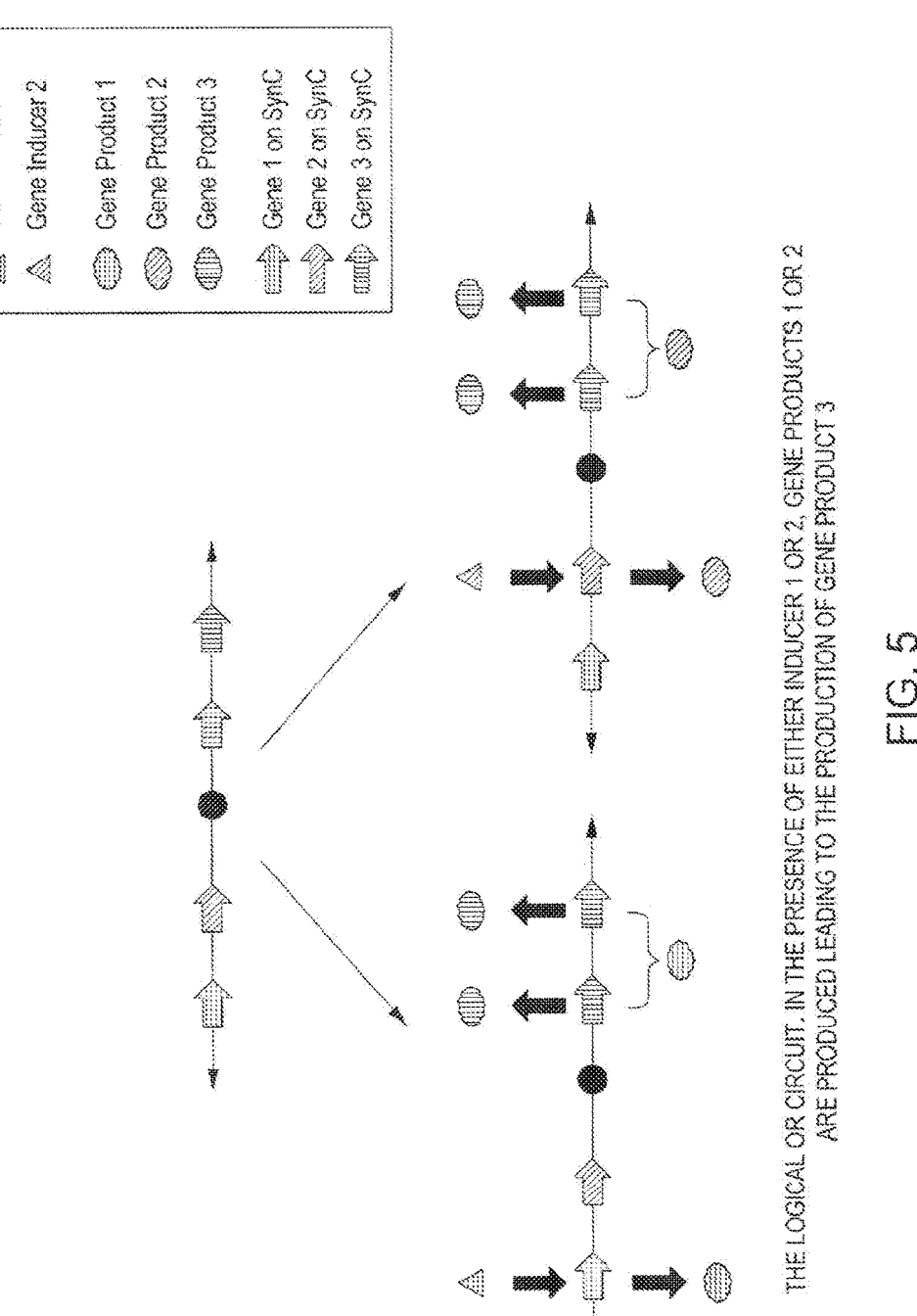
FIG. 5 is a simplified schematic of yet another embodiment of the methods of the present invention, where gene 1 and gene 2 are under the control of different gene regulation control systems, and gene 3 is induced by the gene product of gene 1 or the gene product of gene 2.

In yet another embodiment, a logical "OR" switch is constructed whereby the presence of inducer 1 OR inducer 2 can lead to the expression of gene 1 or gene 2, the production of gene product 1 or gene product 2, and the expression of gene 3 and production of gene product 3. FIG. 5 illustrates this embodiment. Note that the circuits and logical switches ("AND"/"OR") outlined in FIGS. 1-5 may be coordinated to function with endogenous cellular inducers or inducers encoded on additional exogenous DNA (e.g., vectors aside from the synthetic chromosome) residing in the cell. For example, a regulatory control system could be engineered on the platform synthetic chromosome to respond to exogenous signals emanating from the tissue environment, such as an IL-2 responsive promoter driving expression of a factor (e.g. an anti-tumor factor) that would be expressed in a tumor microenvironment.

Synthetic Chromosome Production

Synthetic chromosomes are created in cultured cells. In some embodiments, the cells to be engineered and/or produce the synthetic chromosome can be cells that naturally occur in a subject (human patient, animal or plant) in which the genes or regulatory sequences from the synthetic chromosome will ultimately be expressed. Such cells can be primary-culture cell lines established for the purpose of synthetic chromosome production specific for an individual. In other embodiments, the cells to be engineered and/or produce the synthetic chromosome are from an established cell line. A wide variety of cell lines for tissue culture are known in the art. Examples of cell lines include but are not limited to human cells lines such as 293-T (embryonic kidney), 721 (melanoma), A2780 (ovary), A172 (glioblastoma), A253 (carcinoma), A431 (epithelium), A549 (carcinoma), BCP-1 (lymphoma), BEAS-2B (lung), BR 293 (breast), BxPC3 (pancreatic carcinoma), Cal-27 (tongue), COR-L23 (lung), COV-434 (ovary), CML T1 (leukemia), DUI45 (prostate), DuCaP (prostate), FM3 (lymph node), H1299 (lung), H69 (lung), HCA2 (fibroblast), HEK0293 (embryonic kidney), HeLa (cervix), HL-60 (myeloblast), HMEC (epithelium), HT-29 (colon), HUVEC (umbilical vein epithelium), Jurkat (T cell leukemia), JY (lymphoblastoid), K562 (lymphoblastoid), KBM-7 (lymphoblastoid), Ku812 (lymphoblastoid), KCL22 (lymphoblastoid), KGI (lymphoblastoid), KYO1 (lymphoblastoid), LNCap (prostate), Ma-Mel (melanoma), MCF-7 (mammary gland), MDF-10A (mammary gland), MDA-MB-231, -468 and -435 (breast), MG63 (osteosarcoma), MOR/0.2R (lung), MONO-MAC6 (white blood cells), MRC5 (lung), NCI-H69 (lung), NALM-1 (peripheral blood), NW-145 (melanoma), OPCN/OPCT (prostate), Peer (leukemia), Raji (B lymphoma), Saos-2 (osteosarcoma), Sf21 (ovary), Sf9 (ovary), SiHa (cervical cancer), SKBR3 (breast carcinoma), SKOV-2 (ovary carcinoma), T-47D (mammary gland), T84 (lung), U373 (glioblastoma), U87 (glioblastoma), U937 (lymphoma), VCaP (prostate), WM39 (skin), WT-49 (lymphoblastoid), YAR (B cell), embryonic cell lines, pluripotent cell lines, adult derived stem cells, reprogrammed cell lines, generic animal cell lines of any species or broadly embryonic or reprogrammed cells, patient autologous cell lines, and, in some preferred embodiments, the HT1080 human cell line is utilized. These cell lines and others are available from a variety of sources known to those with skill in the art (see, e.g., the American Type Culture Collection (ATCC) (Manassas, Va.)).

The engineering of synthetic chromosomes to express multiple genes under the control of one or more regulatory control systems is applicable to all of the "top down", "bottom up", engineering of minichromosomes, and induced de novo chromosome generation methods used in the art. The "bottom up" approach of synthetic chromosome formation relies on cell-mediated de novo chromosome formation following transfection of a permissive cell line with cloned α-satellite sequences, which comprise typical host cell-appropriate centromeres and selectable marker gene(s), with or without telomeric and genomic DNA. (For protocols and a detailed description of these methods see, e.g., Harrington, et al., Nat. Genet., 15:345-55 (1997); Ikeno, et al., Nat. Biotechnol., 16:431-39 (1998); Masumoto, et al., Chromosoma, 107:406-16 (1998), Ebersole, et al., Hum. Mol. Gene., 9:1623-31 (2000); Henning, et al., PNAS USA, 96:592-97 (1999); Grimes, et al., EMBO Rep. 2:910-14 (2001); Mejia, et al., Genomics, 79:297-304 (2002); and Grimes, et al., Mol. Ther., 5:798-805 (2002).) Both synthetic and naturally occurring α-satellite arrays cloned into yeast artificial chromosomes, bacterial artificial chromosomes or P1-derived artificial chromosome vectors have been used in the art for de novo synthetic chromosome formation. The products of bottom up assembly can be linear or circular, comprise simplified and/or concatamerized input DNA with an α-satellite DNA based centromere, and typically range between 1 and 10 Mb in size. Bottom up-derived synthetic chromosomes also are engineered to incorporate nucleic acid sequences that permit site-specific integration of target DNA sequence onto the synthetic chromosome.

The "top down" approach of producing synthetic: chromosomes involves sequential rounds of random and/or targeted truncation of pre-existing chromosome arms to result in a pared down synthetic chromosome comprising a centromere, telomeres, and DNA replication origins. (For protocols and a detailed description of these methods see, e.g., Heller, et al., PNAS USA, 93:7125-30 (1996); Saffery, et al., PNAS USA, 98:5705-10 (2001); Choo, Trends Mol. Med., 7:235-37 (2001); Barnett, et al., Nuc. Ac. Res., 21:27-36 (1993); Farr, et al., PNAS USA, 88:7006-10 (1991); and Katoh, et al., Biochem. Biophys. Res. Commun., 321:280-90 (2004).) "Top down" synthetic chromosomes are constructed optimally to be devoid of naturally-occurring expressed genes and are engineered to contain DNA sequences that permit site-specific integration of target DNA sequences onto the truncated chromosome, mediated, e.g., by site-specific DNA integrases.

A third method of producing synthetic chromosomes known in the art is engineering of naturally occurring minichromosomes. This production method typically involves irradiation-induced fragmentation of a chromosome containing a functional, e.g., human neocentromere possessing centromere function yet lacking α-satellite DNA sequences and engineered to be devoid of non-essential DNA. (For protocols and a detailed description of these methods see, e.g., Auriche, et al., EMBO Rep. 2:102-07 (2001); Moralli, et al., Cytogenet. Cell Genet., 94:113-20 (2001); and Carine, et a., Somat. Cell Mol. Genet., 15:445-460 (1989). As with other methods for generating synthetic chromosomes, engineered minichromosomes can be engineered to contain DNA sequences that permit site-specific integration of target DNA sequences.

The fourth and preferred approach for production of synthetic chromosomes involves induced de novo chromosome generation by targeted amplification of specific chromosomal segments. This approach involves large-scale amplification of pericentromeric/ribosomal DNA regions situated on acrocentric chromosomes. The amplification is triggered by co-transfection of excess DNA specific to the percentric region of chromosomes, such as ribosomal RNA, along with DNA sequences that allow for site-specific integration of target DNA sequences (such as attP, attB, attL, attR or the like), and optionally a selectable marker all of which integrate into the pericentric regions of the chromosomes. (For protocols and a detailed description of these methods see, e.g., Csonka, et al., J. Cell Sci 113:3207-16 (2002); Hadlaczky, et al., Curr. Opini. Mol. Ther., 3:125-32 (2001); and Lindenbaum and Perkins, et al., Nuc. Ac. Res., 32 (21):e172 (2004).) During this process, targeting to the pericentric regions of acrocentric chromosomes with co-transfected DNA induces large-scale chromosomal DNA amplification, duplication/activation of centromere sequences, and subsequent breakage and resolution of dicentric chromosomes resulting in a "break-off" satellite DNA-based synthetic chromosome containing multiple site-specific integration sites.

An integral part of the synthetic platform chromosome technology is the site-specific recombination system that allows the "loading" or placement of selected regulatory control systems and genes onto the synthetic chromosome. In preferred embodiments of the present invention, the synthetic platform chromosome comprises multiple site-specific recombination sites into each of which one or several genes of interest may be inserted. Any known recombination system can be used, including the Cre/lox recombination system using CRE recombinase from E. coli phage P1 (see, e.g., Sauer, Methods in Enzymology, 225: 890-900 (1993) and U.S. Pat. No. 5,658,772); the FLP/FRT system of yeast using the FLP recombinase from the 2µ episome of Saccharomyces cerevisiae (see, e.g., Cox, PNAS U.S.A., 80:4223 (1983) and U.S. Pat. No. 5,744,336); the resolvases, including Gin recombinase of phage Mu (Weser et al., Mol Gen Genet., 230:170-176 (1991)), Cin, Hin, αδ, Tn3; the Pin recombinase of E. coli (see, e.g., Enomoto et al., J Bacteriol., 6:663-668 (1983)); the R/RS system of the pSR1 plasmid of Zygosaccharomyces rouxii (see, e.g., Araki et al., J. Mol. Biol., 225:25-37 (1992)); site-specific recombinases from Kluyveromyces drosophilarium (see, e.g., Chen et al., Nucleic Acids Res., 314:4471-4481 (1986)) and Kluyveromyces waltii (see, e.g., Chen et al, J. Gen. Microbiol., 138:337-345 (1992)); and other systems known to those of skill in the art; however, recombination systems that operate without the need for additional factors—or by virtue of mutation do not require additional factors—are preferred. In one exemplary embodiment, a method is provided for insertion of nucleic acids into the synthetic platform chromosome via sequence-specific recombination using the recombinase activity of the bacteriophage lambda integrase.

Lambda phage-encoded integrase (designated "Int") is a prototypical member of the integrase family. Int effects integration and excision of the phage into and out of the E.

*coli* genome via recombination between pairs of attachment sites designated attB/attP and attL/attR. Each att site contains two inverted 9 base pair core Int binding sites and a 7 base pair overlap region that is identical in wild-type att sites. Int, like the Cre recombinase and Flp-FRT recombinase systems, executes an ordered sequential pair of strand exchanges during integrative and excisive recombination. The natural pairs of target sequences for Int, attB and attP or attL and attR are located on the same or different DNA molecules resulting in intra- or inter-molecular recombination, respectively. For example, intramolecular recombination occurs between inversely oriented attB and attP, or between attL and attR sequences, respectively, leading to inversion of the intervening DNA segment. Though wild-type Int requires additional protein factors for integrative and excisive recombination and negative supercoiling for integrative recombination, mutant Int proteins do not require accessory proteins to perform intramolecular integrative and excisive recombination in co-transfection assays in human cells (see Lorbach et al., J Mol. Biol., 25 296:1175-1181 (2000)) and are preferred for the methods of the present invention.

Delivery Vectors to Deliver Multiple Genes in the Biosynthetic Pathway

The choice of delivery vector to be used to deliver or "load" the multiple regulatory control systems and multiple genes onto the synthetic platform chromosome will depend upon a variety of factors such as the type of cell in which propagation is desired. The choice of appropriate delivery vector is well within the skill of those in the art, and many vectors are available commercially. To prepare the delivery vector, one or more genes under the control of one or more regulatory control systems are inserted into a vector, typically by means of ligation of the gene sequences into a cleaved restriction enzyme site in the vector. Alternatively, the desired nucleotide sequences can be inserted by homologous recombination or site-specific recombination. Typically homologous recombination is accomplished by attaching regions of homology to the vector on the flanks of the desired nucleotide sequence (e.g., cre-lox, att sites, etc.). Nucleic acids containing such sequences can be added by, for example, ligation of oligonucleotides, or by polymerase chain reaction using primers comprising both the region of homology, and a portion of the desired nucleotide sequence. Exemplary delivery vectors that may be used include but are not limited to those derived from recombinant bacteriophage DNA, plasmid DNA or cosmid DNA. For example, plasmid vectors such as pBR322, pUC 19/18, pUC 118, 119 and the M13 mp series of vectors may be used. Bacteriophage vectors may include λgt10, λgt11, λgt18-23, λZAP/R and the EMBL series of bacteriophage vectors. Cosmid vectors that may be utilized include, but are not limited to, pJB8, pCV 103, pCV 107, pCV 108, pTM, pMCS, pNNL, pHSG274, COS202, COS203, pWE15, pWE16 and the charomid 9 series of vectors. Additional vectors include bacterial artificial chromsomes (BACs) based on a functional fertility plasmid (F-plasmid), yeast artificial chromosomes (YACs), and P1-derived artificial chromsomes, DNA constructs derived from the DNA of P1 bacteriophage (PACS). Alternatively and preferably, recombinant virus vectors may be engineered, including but not limited to those derived from viruses such as herpes virus, retroviruses, vaccinia virus, poxviruses, adenoviruses, lentiviruses, adeno-associated viruses or bovine papilloma virus. BAC vectors are the preferred delivery vectors for the present invention, due to their ability to carry large amounts of nucleic acids, i.e., multiple genes. Alternatively, the genes under control of the regulatory control systems may be loaded onto the synthetic platform chromosome via sequential loading using multiple delivery vectors; that is, a first gene under control of a first regulatory control system may be loaded onto the synthetic platform chromosome via a first delivery vector, a second gene under control of a second regulatory control system may be loaded onto the synthetic platform chromosome via a second delivery vector, and so on. Perkins and Greene, U.S. Ser. No. 62/321,711 filed 12 Apr. 2016, describe sequential loading of genes onto a synthetic platform chromosome using multiple delivery vectors while recycling a single selectable marker.

A selectable marker operative in the expression host optionally may be present to facilitate selection of cells containing the delivery vector. In addition, the delivery vector may include additional elements; for example, the delivery vector may have one or two replication systems; thus allowing it to be maintained in organisms, for example in mammalian cells for expression and in a prokaryotic host for cloning and amplification.

Using lambda integrase mediated site-specific recombination—or any other recombinase-mediated site-specific recombination—the genes under regulatory control are introduced or "loaded" from the delivery vector onto the synthetic platform chromosome. Because the synthetic platform chromosome contains multiple site-specific recombination sites, the multiple genes may be loaded onto a single synthetic platform chromosome. The recombinase that mediates the site-specific recombination may be delivered to the cell by encoding the gene for the recombinase on the delivery vector, or purified or encapsulated recombinase protein a delivered to a recipient cells using standard technologies. Each of the multiple genes may be under the control of its own regulatory control system; alternatively, the expression of the multiple genes may be coordinately regulated via viral-based or human internal ribosome entry site (IRES) elements (see, e.g., Jackson et al., Trends Biochem Sci. 15: 477-83 (1990); and Oumard et al., Mol. Cell. Biol. 20: 2755-2759 (2000)) or 2A self-cleaving peptides (See, Kim, et al., PLoS ONE, 6 (4), e18556. http://doi.org/10.1371/journal.pone.0018556). Additionally, using IRES type elements or 2A peptides linked to a fluorescent marker downstream from the target genes—e.g., green, red or blue fluorescent proteins (GFP, RFP, BFP)—allows for the identification of synthetic platform chromosomes expressing the integrated target genes. Alternatively or in addition, site-specific recombination events on the synthetic chromosome can be quickly screened by designing primers to detect integration by PCR.

Component Delivery into the Synthetic Chromosome Production Cells

The components appropriate for synthetic chromosome production and the delivery vector(s) can be delivered to the recipient cells by any method known in the art. The terms transfection and transformation refer to the taking up of exogenous nucleic acid, e.g., an expression vector, by a host cell whether or not any coding sequences are, in fact, expressed. Numerous methods of transfection are known to the ordinarily skilled artisan, for example, by *Agrobacterium*-mediated transformation, protoplast transformation (including polyethylene glycol (PEG)-mediated transformation, electroporation, protoplast fusion, and microcell fusion), lipid-mediated delivery, liposomes, electroporation, sonoporation, microinjection, particle bombardment and silicon carbide whisker-mediated transformation and combinations thereof (see, e.g., Paszkowski, et al., EMBO J., 3:2717-2722 (1984); Potrykus, et al., Mol. Gen. Genet., 199:169-177 (1985); Reich, et al., Biotechnology, 4:1001-1004 (1986); Klein, et al., Nature, 327:70-73 (1987); U.S. Pat. No. 6,143,949; Paszkowski, et al., in *Cell Culture and Somatic Cell Genetics of Plants*, Vol. 6, Molecular Biology of Plant Nuclear Genes, (Schell and Vasil, eds., Academic Publishers 1989); and Frame, et al., Plant J., 6:941-948 (1994)); direct uptake using calcium phosphate (Wigler, et al., Proc. Natl. Acad. Sci. U.S.A., 76:1373-1376 (1979)); polyethylene glycol (PEG)-mediated. DNA uptake; lipofection (see, e.g., Strauss, Meth. Mol. Biol., 54:307-327 (1996)); microcell fusion (Lambert, Proc. Natl. Acad. Sci. U.S.A., 88:5907-5911 (1991); U.S. Pat. No. 5,396,767; Sawford, et al., Somatic Cell Mol. Genet., 13:279-284 (1987); Dhar, et al., Somatic Cell Mol. Genet., 10:547-559 (1984); and McNeill-Killary, et al., Meth. Enzymol., 254: 133-152 (1995)); lipid-mediated carrier systems (see, e.g., Teifel, et al., Biotechniques, 19:79-80 (1995); Albrecht, et al., Ann. Hematol., 72:73-79 (1996); Holmen, et al., In Vitro Cell Dev. Biol. Anim., 31:347-351 (1995); Remy, et al., Bioconjug. Chem., 5:647-654 (1994); Le Bolch, et al., Tetrahedron Lett., 36:6681-6684 (1995); and Loeffler, et al., Meth. Enzymol., 217:599-618 (1993)); or other suitable methods. Methods for delivery of synthetic chromosomes also are described in U.S. application Ser. No. 09/815,979. Successful transfection is generally recognized by detection of the presence of the heterologous nucleic acid within the transfected cell, such as, for example, any visualization of the heterologous nucleic acid, expression of a selectable marker or any indication of the operation of the synthetic platform chromosome or the delivery vector within the host cell. For a description of delivery methods useful in practicing the present invention, see U.S. Pat. Nos. 5,011,776; 5,747,308; 4,966,843; 5,627,059; 5,681,713; Kim and Eberwine, Anal. Bioanal. Chem. 397 (8): 3173-3178 (2010).

Visualization, isolation, and Transfer to Recipient Immune Cells

The production and loading of the synthetic platform chromosomes of the present invention can be monitored by various methods. Lindenbaum and Perkins, et al., Nucleic Acid Research, 32 (21):e172 (2004) describe the production of a mammalian satellite DNA-based Artificial Chromosome Expression (ACE) System using prior art technology. In this prior art system, conventional single-color and two-color FISH analysis and high-resolution FISH were carried out using PCR-generated probes or nick-translated probes. For detection of telomere sequences, mitotic spreads were hybridized with a commercially-obtained peptide nucleic acid probe. Microscopy was performed using fluorescent microscopy. Alternatively, Perkins and Greene, PCT/US16/17179 filed 9 Feb. 2016, describes compositions and methods to allow one to monitor formation of synthetic chromosomes in real-time via standardized fluorescent technology using two labeled tags: one labeled tag specific to endogenous chromosomes in the cell line used to produce the synthetic platform chromosomes, and one differently-labled tag specific to a sequence on the synthetic chromosome that is to be produced.

Isolation and transfer of synthetic chromosomes typically involves utilizing microcell mediated cell transfer (MMCT) technology or dye-dependent, chromosome staining with subsequent flow cytometric-based sorting. In the MMCT technique, donor cells are chemically induced to multinucleate their chromosomes with subsequent packaging into microcells and eventual fusion into recipient cells. Establishing that the synthetic chromosomes have been transferred to recipient cells is carried out with drug selection and intact delivery of the transferred chromosome confirmed by FISH. Alternatively, flow cytometric-based transfer can be used. For flow cytometric-based transfer, mitotically arrested chromosomes are isolated and stained with DNA specific dyes and flow sorted based on size and differential dye staining. The flow-sorted chromosomes are then delivered into recipient cells via standard DNA transfection technology, and delivery of intact chromosomes is determined by FISH. In yet another alternative, in addition to the visualization and monitoring of synthetic chromosome production described in Perkins and Greene, PCT/US16/17179 filed 9 Feb. 2016, the synthetic chromosome tags can be used to isolate the synthetic chromosomes from the synthetic chromosome production cells via flow cytometry, as well as to monitor the transfer of the synthetic chromosomes into recipient cells.

EXAMPLES

Example 1: De Novo Generation of Satellite DNA-Based Artificial Chromosome

For de novo production of synthetic chromosomes, exogenous DNA sequences were introduced into HT1080 synthetic chromosome production cell line, and, upon integration into the pericentric heterochromatic regions of acrocentric chromosomes, a large-scale amplification of the short arms of the acrocentric chromosome (rDNA/centromere region) was triggered. During the amplification event, the centromere was duplicated resulting in a dicentric chromosome with two active centromeres. Subsequent mitotic events resulted in cleavage and resolution of the dicentric chromosome, leading to a breakoff of approximately 20-120 Mb in size comprised predominantly of satellite repeat sequences with subdomains of coamplified transfected transgene that may also contain amplified copies of rDNA. The newly-generated synthetic chromosome is validated by observation of fluorescent chromosome painting (or FISH), via an endogenous chromosome tag and a synthetic chromosome tag that was engineered into the HT1080 synthetic chromosome production cell line.

The day before transfection, the HT1080 synthetic chromosome production cell line cells were split to a density of approximately 2.0 to $8.0 \times 10^4$ adherent cells into 24-well tissue culture dishes, and the vectors comprising the exogenous DNA were purified (e.g., using a Qiagen EndoFree Plasmid Maxi Kit), linearized, and the concentration of the vectors was determined for transfection. The cultured HT1080 cells were fed 3-5 hours before transfection. 225 ng of pSTV28HurDNA vector and 12.5 ng p15A7248lacEF1attPPuro vector per 24-well semiconfluent tissue culture dish was used to transfect the HT1080 cells using standard transfection reagents, e.g., ThermoFisher Lipofectamine LTX, Promega's Viafect, or Invitrogen's Calcium Phosphate Transfection Kit. The pSTV28HurDNA vector comprises the ribosomal DNA sequences. The p15A7248lacEF1attPPuro vector comprises the components for the site-specific recombination system, the LacO repeats and an ampicillin and a puromycin resistance gene. Cells were maintained for 1-3 days post-transfection at which point they were trypsinized and replated onto a 10 cm dish. Selective medium was added to the 10 cm dish at the time of plating or 1-3 days post plating. Selective conditions were maintained for 10-21 days with media changed every 2-3 days. Antibiotic resistant clones were picked when a colony reached 2-3 mm in diameter. Colonies that were well separated are preferred. Cells were removed by use of a cloning cylinder and trypsin, and transferred to a 24-well plate for expansion.

Example 2: Creating TET Repressor and Cumate Repressor Delivery Vectors

Figure 6:
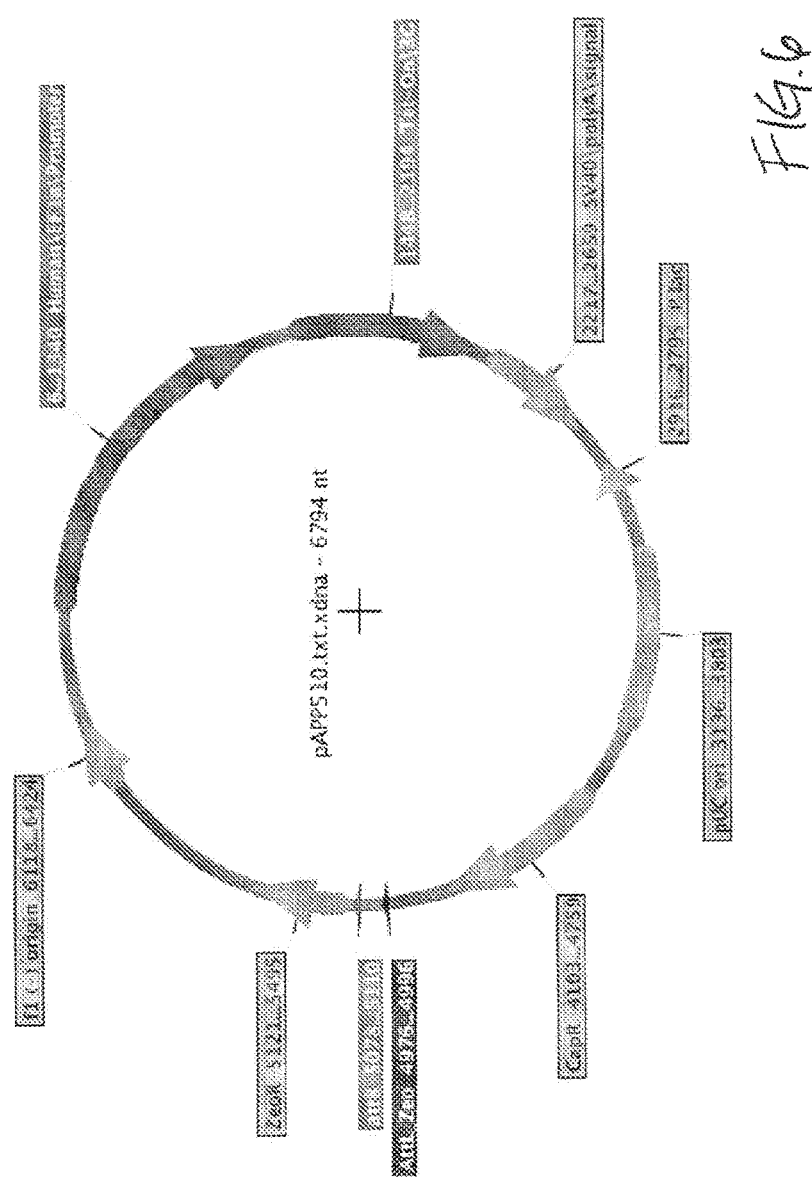
FIG. 6 is a simplified schematic of the TET regulator delivery vector.

One embodiment of a regulable promoter system to be incorporated on the synthetic platform chromosome is the TET-ON, doxycycline inducible expression system (Clontech, Inc.). A pAPP500 vector was used as the backbone delivery vector to insert the TET-ON transcriptional regulator onto the synthetic chromosome. In brief, the pEF1alpha-Tet3G transcriptional regulator was isolated by restriction digest (BsrGI and HindIII), then treated to fill the 5' ends and ligated into pAPP500 digested with EcoRV. The resulting plasmid vector (pAPP510; FIG. 6: in pApp590, the following elements are present: SV40\polyA/signal=SV40 poly A; attB, AttL_Zeo=site specific recombination sites; Human/EF1a/Pr=promoter; Tet-On/3G=transcriptional regulator; f1 origin=origin of replication; ZeoR=zeocin resistance) contains a promoterless zeocin resistance marker gene encoded behind the attB recombination site for targeting onto the synthetic platform chromosome, and the TET-ON transcriptional regulator.

Figure 7:
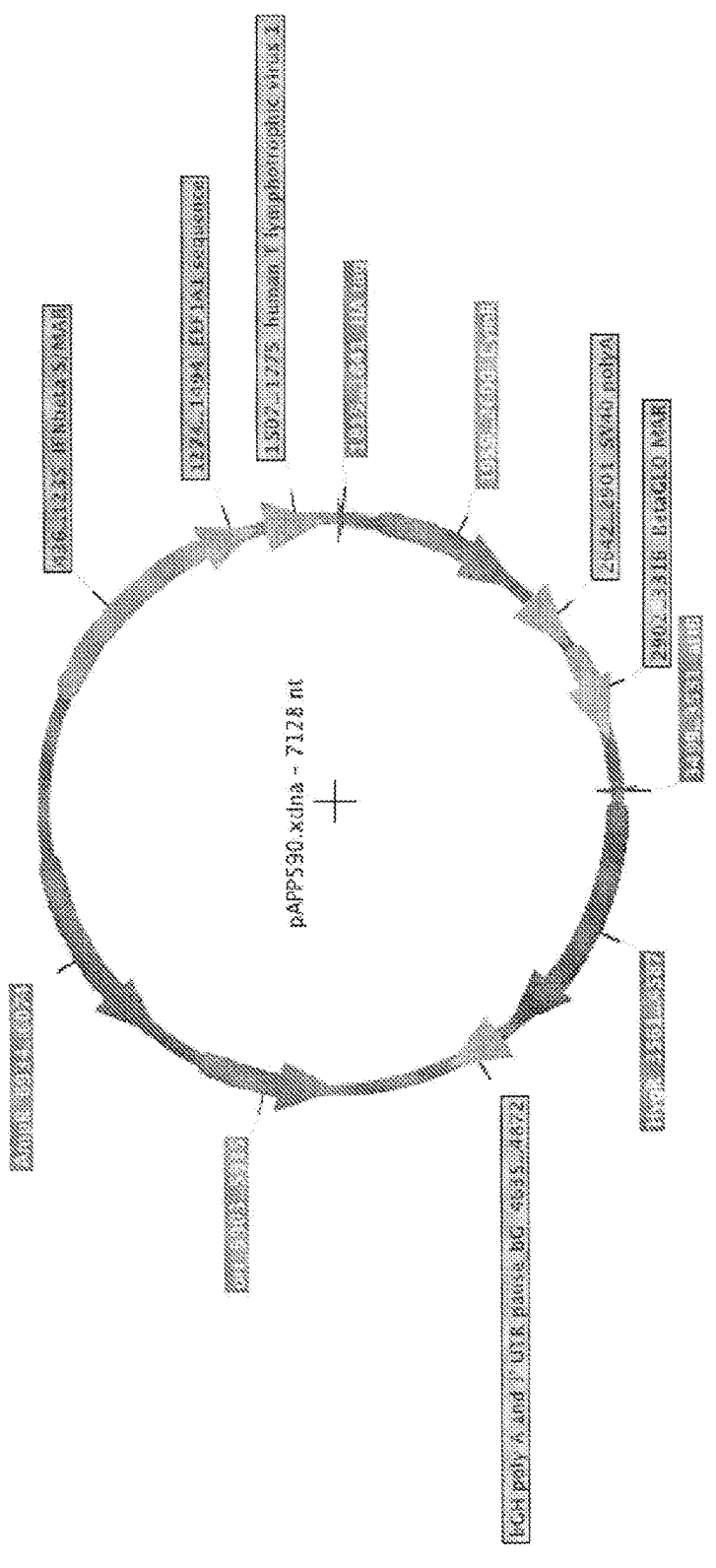
FIG. 7 is a simplified schematic of the Cumate regulator delivery vector.

A second regulable gene expression system (Cumate-ON) will be integrated onto the TET-ON containing synthetic platform chromosome as a "proof of principle" for the production of multiple, regulable anticancer antibody fragments. The Cumate-ON transcriptional regulator (CymR) was cloned into pAPP570. pAPP570 contains a promoterless hygromycin resistance marker gene encoded behind the attB recombination site. In brief, pUCMAR1CymR, containing the Cumate-ON transcriptional regulator, was digested with SalI, then treated with Klenow to fill the 5' end and ligated to pAPP570 that has been digested with HindIII and XhoI and Klenow treated. The resulting plasmid vector (pAPP590; FIG. 7: in pApp590, the following elements are present: SV40\polyA/signal=SV40 poly A; attB=site specific recombination site; EF1A1 sequence=promoter; AmpR, HygR, CymR=drug resistance genes; ori=origin of replication; HA tag=human influcenza hemagglutinin epitope tag; bGH poly A and 3' UTR pause=poly A; MAR=matrix attachment region.)) contains a promoterless hygromycin resistance marker gene encoded behind the attB recombinations site for targeting onto the synthetic platform chromosome and the Cumate-ON transcriptional regulator.

Example 3: Loading the TET-ON and Cumate-ON Transcriptional Regulators onto the Synthetic Chromosome The pAPP510 and pAPP590 vectors are used as the delivery vectors to sequentially insert the TET-ON transcriptional regulator and Cumate-ON transcriptional regulator, respectively, onto the synthetic chromosome. On day 0, the recipient cell line (e.g., HT1080) containing the synthetic chromosome (hSynC) is seeded at ~4E4 cells/well of a 24-well dish, such that the wells are ~70% confluent on Day 1. The cells are incubated overnight at 37° C., 5% CO$_2$, in appropriate medium (e.g., DMEM+10% FC3 for HT1080). On day 1, following the manufacturer's instructions (Fisher Scientific, Lipofectamine LTX with Plus reagent) both the delivery vector (e.g. pAPP510) and the plasmid encoding the recombination protein (e.g. pCXLamIntR) are transfected into the HT1080 cells. Transfections are performed in duplicate so that a comparison of drug selection and direct cell sorting can be made. The Lipofectamine LTX is diluted in Opti-MEM medium (Gibco; 1.5 ul LTX/50 ul Opti-MEM for each well of the 24-well dish to be transfected), and 250 ng DNA is added to 50 ul diluted LTX in Opti-MEM (e.g. 125 ng pAPP510 plasmid and 125 ng pCXLamIntR per well). 0.25 ul PLUS reagent is added to each ~50 ul DNA-LTX-Opti_MEM sample, and each sample is incubated at room temperature for 5 minutes. The medium is then removed from the cells plated on Day 0 and fresh medium is used to replace the medium during the 5 minute incubation. DNA-lipid complexes are added to the cells and incubated at 37° C., 5% CO$_2$, in appropriate medium.

On days 2-24, drug selection is performed. The cells from one of the duplicate 24-well wells are trypsinized and transferred to a 10 cm dish with fresh medium containing drug selection (e.g., zeocin 100 ug/ml). The cells are then incubated at 37° C., 5% CO$_2$, in appropriate medium, and monitored for colony formation. The medium is replaced approximately every 72 hours. When distinct colonies are formed (approximately 10 days), each colony is isolated by a glass cylinder, trypsinized and transferred to a well of a 24-well dish. These "clones" are then expanded in culture until sufficient cells are available to place the clone in cold storage and isolate genomic DNA (approximately 2 weeks; Promega Wizard SV Genomic DNA Purification) for PCR analysis.

Integration of the delivery vector containing the gene/DNA elements of interest is identified by the production of a unique PCR product that spans the recombination site between the synthetic chromosome and the delivery vector (pAPP510) using appropriate PCR primers. Negative control PCR reactions of water and host genomic DNA (e.g. HT1080) are performed in conjunction with the test genomic DNA samples.

Upon identification of candidate clones containing the TET-ON transcriptional regulator properly loaded onto the synthetic chromosome tests are performed to assess the ability of the TET-ON transcriptional regulator to control expression of a secreted luciferase under the control of a TRE-tight promoter (TetP). Candidate clones demonstrating low luciferase expression in medium without doxycycline (the TET-ON inducer) and high expression in the presence of doxycycline are placed in long term cold storage. The best candidate clone, designated "A1", is chosen for delivery of the Cumate-ON transcriptional regulator. This system demonstrates robust, doxycycline-dependent induction of a transiently transfected luciferase gene reporter under regulatory control of a TET-ON promoter when residing on a synthetic platform chromosome The Cumate-ON transcriptional regulator will be delivered to the A1 cell line containing the TET-ON transcriptional regulator. On day 0, the recipient cell line (e.g., HT1080-A1) containing the synthetic chromosome (hSynC) previously loaded with the TET-ON transcriptional regulator is seeded at ~4E4 cells/well of a 24-well dish, such that the wells are ~70% confluent on Day 1. The cells are incubated overnight at 37° C., 5% CO$_2$, in appropriate medium (e.g., DMEM+10% FC3 for HT1080). On day 1, following the manufacturer's instructions (Fisher Scientific, Lipofectamine LTX with Plus reagent) both the delivery vector (e.g. pAPP590) and the plasmid encoding the recombination protein (e.g. pCXLamIntR) are transfected into the HT1080-A1 cell line. Transfections are performed in duplicate so that a comparison of drug selection and direct cell sorting can be made. The Lipofectamine LTX is diluted in Opti-MEM medium (Gibco; 1.5 ul LTX/50 ul Opti-MEM for each well of the 24-well dish to be transfected), and 250 ng DNA is added to 50 ul diluted LTX in Opti-MEM (e.g. 125 ng pAPP590 plasmid and 125 ng pCXLamIntR per well). 0.25 ul PLUS reagent is added to each ~50 ul DNA-LTX-Opti_MEM sample, and each sample is incubated at room temperature for 5 minutes. The medium is then removed from the cells plated on Day 0 and fresh medium is used to replace the medium during the 5 minute incubation. DNA-lipid complexes are added to the cells and incubated at 37° C., 5% $CO_2$, in appropriate medium.

On days 2-24, drug selection is performed. The cells from one of the duplicate 24-well wells are trypsinized and transferred to a 10 cm dish with fresh medium containing drug selection (e.g., hygromycin at 100 ug/ml). The cells are then incubated at 37° C., 5% $CO_2$, in appropriate medium, and monitored for colony formation. The medium is replaced approximately every 72 hours. When distinct colonies are formed (approximately 10 days), each colony is isolated by a glass cylinder, trypsinized and transferred to a well of a 24-well dish. These "clones" are then expanded in culture until sufficient cells are available to place the clone in cold storage and isolate genomic DNA (approximately 2 weeks; Promega Wizard SV Genomic DNA Purification) for PCR analysis.

Integration of the delivery vector containing the gene/DNA elements of interest is identified by the production of a unique PCR product that spans the recombination site between the synthetic chromosome and the delivery vector (pAPP590) using appropriate PCR primers. Negative control PCR reactions of water and host genomic DNA (e.g. A1) are performed in conjunction with the test genomic DNA samples.

Upon identification of candidate clones containing the Cumate-ON transcriptional regulator properly loaded onto the synthetic chromosome tests were performed to assess the ability of the Cumate-ON transcriptional regulator to control expression of a secreted luciferase under the control of a Cumate responsive promoter (CMV+CuO promoter). Candidate clones demonstrating low luciferase expression in medium without cumate (the Cumate-ON inducer) and high expression in the presence of cumate will be placed in long term cold storage.

Example 4: Expression of Multiple scFv Fragments from Two Separate Inducible Promoter Systems Clinical experience shows that multi-targeted approaches to cancer therapy and infectious disease are generally superior to single agent treatments. Based on their plasticity and robustness, mesenchymal stem cells (MSC) have been implicated as a novel therapeutic modality for the treatment of cancer and infectious disease. As such, bioengineered MSCs, or other additional stem cell populations, hold exceptional utility as novel weapons against cancer and infectious disease for which effective therapies are lacking. Furthermore, the localized delivery of therapeutic factors delivered via stem cell-based therapy may circumvent pharmacological limitations associated with systemic delivery of particularly toxic agents. The combination of synthetic platform chromosomes engineered to deliver multiple and regulable therapeutic factors has enormous potential as a therapeutic approach that can be tailored to target different disease states.

Single-chain fragment variable (scFv) proteins are attractive therapeutic agents for targeted delivery of cytostatic/cytotoxic bioreagents. scFvs are small antigen-binding proteins made up of antibody VH and VL domains that can exquisitely target and penetrate tumor beds or target infectious diseases agents. The small size of scFvs makes them amenable to fusing with cytotoxic proteins for immunotoxin-based gene therapy. The regulable production of multiple scFvs from the synthetic platform chromosome both in vitro and in vivo is demonstrated utilizing a number of select tumor maker scFvs.

Four scFv DNA clones targeting Her2 (ErbB2; scFv1 in FIG. 8), basigen (scFv2 in FIG. 8), c-kit (scFv3 in FIG. 8), and carcinoembryonic antigen (CEA; scFv4 in FIG. 8) are expressed. All four of these clones are obtained from appropriate commercial vendors (Source BioScience, Inc., Addgene). The scFv encoding DNA regions are amplified by PCR and N-terminal fusions of each are made with luciferase reporter constructs (New England Biolabs, Inc). scFv1 and scFv2 are fused to the secreted *Gaussia* luciferase reporter and scFv3 and scFv4 are fused to the secreted *Cypridina* luciferase reporter. The utilization of these two ultrasensitive secreted luciferase reporters permits monitoring of expression in a dual assay format as each luciferase utilizes a unique substrate (i.e. the detection of one luciferase can be measured without any cross-reactivity from the presence of the other in a given sample). The scFv1 and scFv2 are cloned and placed under the control of the TET-ON promoter (TetP in FIG. 8). For multiple, regulable expression the Cumate Switch ON system (system commercially available from System Biosciences Inc.) is also utilized. Similar to the TET-ON system, the Cumate Switch On system works by the binding of the Cym repressor (cymR; originally derived *Pseudomonas*) to cumate operator sites downstream of the CMV5 promoter to block transcription. In the presence of cumate, the repression is relieved allowing for transcription. The Cumate Switch ON system has been used extensively in in vitro applications and is comparable to performance to the TET-ON system. scFv3 and scFv4 CLuc fusions are placed under the control of the Cumate Switch On promoter. Polyadenylation signals and strong transcription termination sequences are placed downstream of all scFv expression cassettes.

Figure 8:
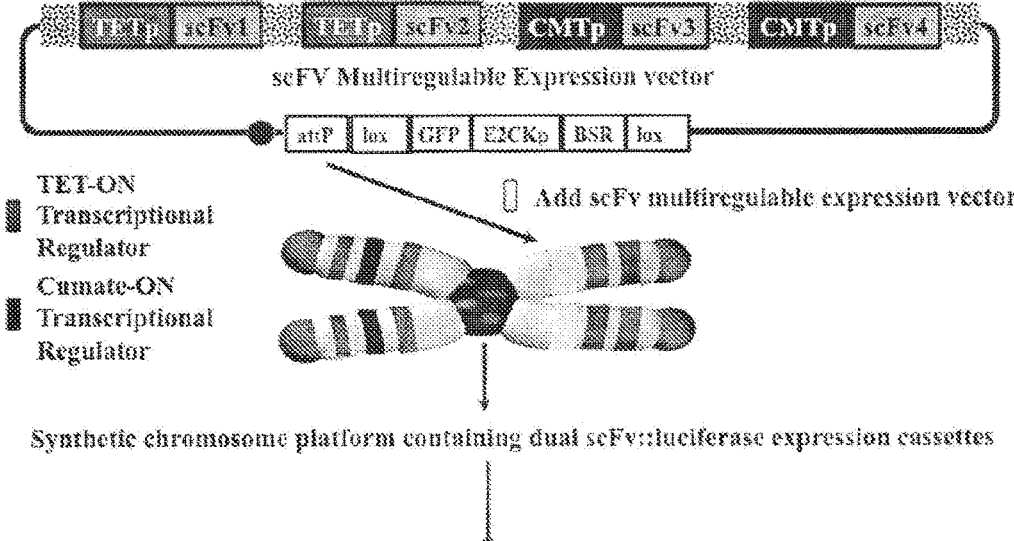
FIG. 8 is a simplified schematic of the loading of an scFV multiregulable expression vector onto a synthetic chromosome.
Figure 9:
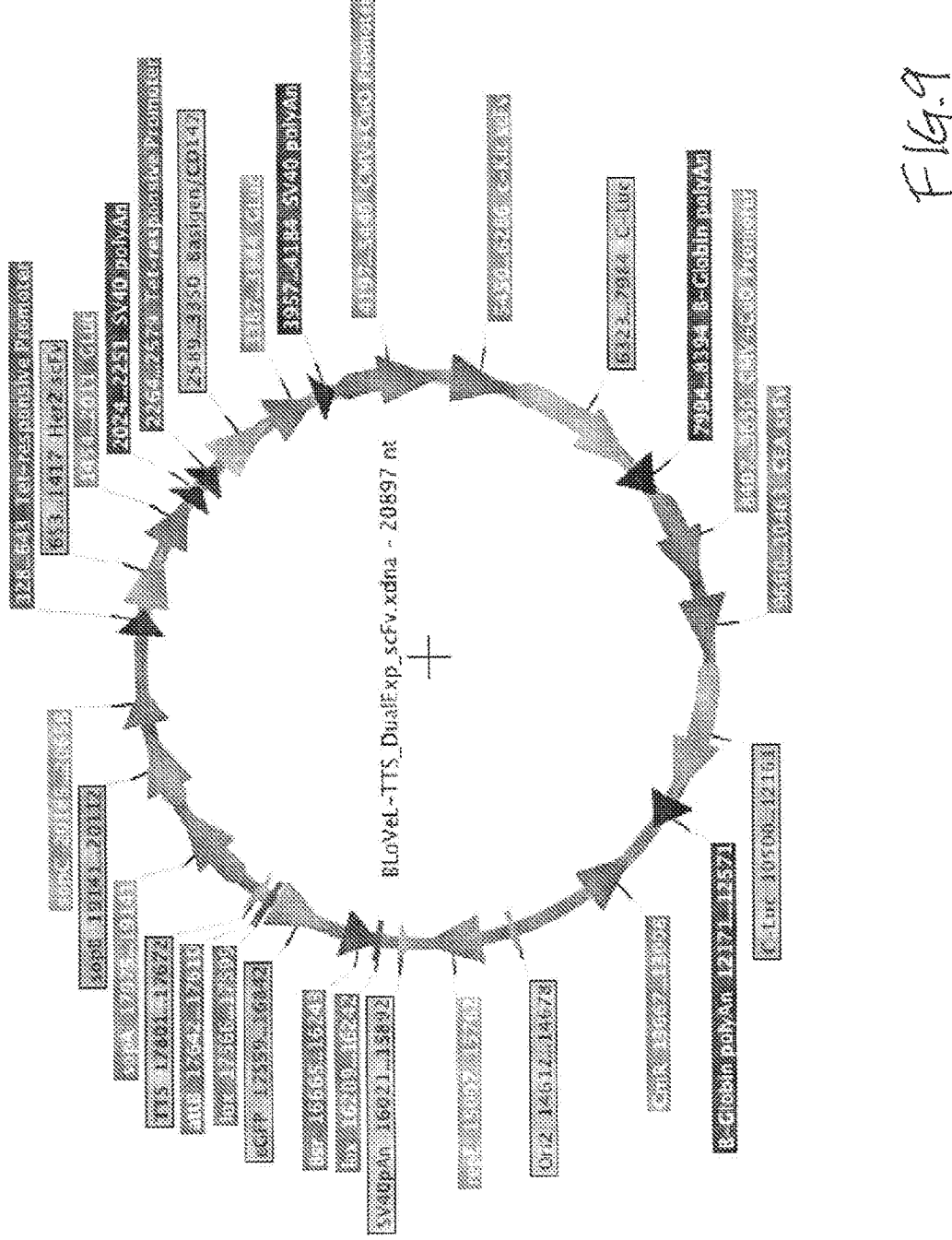
FIG. 9 is a simplified schematic of the multitregulable scFv expression delivery vector.

The scFv expression cassettes are cloned in tandem onto a BAC-derived pAPP delivery vector with each expression cassette separated by matrix attachment regions to promote optimal expression and to block transcriptional read through from one cassette to another (hashed boxes in FIG. 8). The BAC-derived pAPP delivery vector is retrofitted to contain the attB recombination sequence upstream of a GFP-(BSR in FIG. 8) fusion protein cassette. Blasticidin resistance is selectable in bacteria due to the presence of the bacterial E2CK promoter within an engineered intron of the GFP-BSR fusion. Furthermore, the GFP-BSR cassette is flanked by lox sites to permit recycling of the GFP-BSR selectable marker. This vector, the scFv multi-regulable expression BAC, contains all of the scFV expression cassettes and is approximately 21 Kbp in size (pBLoVeL-TSS_DualExp_scFv; FIG. 9: in BLoVeL-TSS_Dual Exp, the following elements are present: sopA, sopB, and sopC=plasmid partitioning proteins; SV40pAn, B-Globin poly An=poly A; TTS=transcription termination signal; attB=site specific recombination site; lox=site specific recombination site; eGFP=fluorescent protein; Bsr=blasticidin resistance gene; repE=replication initiation site; Ori2=origin of replication; CmR=chloramphenicol resistance gene; polyAn=poly A; Her 2 scFv, c-Kit scFv, CEA scFv=single-chain fragment variable (scFv) proteins; Tet-responsive promoter or CMV+CuO promoter=inducible promoters)).

The scFv expression BACs are engineered onto the synthetic platform chromosome by lambda integrase mediated recombination. One additional feature of the expression BAC is the presence of strong transcriptional termination signal (TTS; black circle in FIG. 8) that is placed 5' with respect to the attB sequence. The presence of the TTS is tested as to whether the element prevents spurious transcription through the GFP cassette leading to the presence of GFP+ cells that are not on the synthetic platform chromosome. If the presence of the TTS blocks spurious transcription through the GFP gene, then a higher percentage of GFP+ cells should reflect the site-specific recombination of the expression BAC onto the synthetic platform chromosome. If this is observed, then 48-72 hours post-transfection GFP+ cells are single cell cloned by flow cytometry/cell sorting circumventing need for drug selection in obtaining synthetic platform chromosome engineered cells. This potentially saves 1-3 weeks of time in obtaining the desired synthetic platform chromosome clones and increase engineering efficiency.

After clones are expanded, confirmation of the placement of the expression BAC on the synthetic platform chromosome is accomplished by PCR for the presence of the attR/attL recombination junctions. From previous work on engineering the platform chromosome with synthetic platform chromosome delivery vectors it has been observed that once clones are identified, there appears to be a distribution of the number of targeted vectors placed onto the synthetic platform chromosome. From copy number analysis, some clones contain a single copy of the delivery vector, some carry approximately ten copies, and some carry over twenty copies the delivery vector on the synthetic platform chromosome, qPCR analysis is used for copy number analysis for synthetic platform chromosome engineered clones containing a single copy of the scFv expression BAC (addition of 21 Kbp of DNA), clones containing approximately ten copies (addition of 210 Kbp of DNA), and clones that contain greater than twenty copies of the scFv expression BAC (>420 Kbp of DNA; termed "low", "medium", and "high" respectively).

Example 5: In Vitro Testing for scFv Production

Representative low, medium, and high copy synthetic platform chromosome clones are transferred into the mouse (Balb/c) D1 MSC line and delivery of intact synthetic chromosome engineered platforms are confirmed by FISH analysis. At this point, the synthetic platform chromosome engineered cell lines are tested in vitro for the regulated production of the select scFvs. Secreted scFv production levels are tested under four conditions: 1) without doxycycline, without cumate, 2) with doxycycline, with cumate, 3) without doxycycline, with cumate, and 4) with doxycycline, without cumate for each of the low, medium and high cell lines. Both the scFv-GLuc and scFv-CLuc fusions are measured in the samples using the *Gaussia* and *Cypridina* luciferase assay systems according to the manufacturer's instructions (New England Biolabs, Inc.). Samples are tested at time zero with respect to the addition of inducing signal (doxycycline and/or cumate or vehicle only) with subsequent samples assayed at 6 hour, 12 hour, 24 hour, and 48 hour time points. At the 48 hour time point, cells are harvested for RNA isolation and the presence or absence of each unique expressed scFv is determined by RT-PCR using primers specific to Her2 (scFv1), basigen (scFv2), c-Kit (scFv3), and CEA (scFv4).

Example 6: In Vivo Testing for scFv Production

For determining scFv production in vivo, $1 \times 10^7$ cells containing a synthetic platform chromosome with either the low, medium or high copy scFv expression cassette are injected subcutaneously into the flank of 6 to 8 week-old Balb/c mice. Similar to the in vitro testing, secreted scFv production levels are tested under four conditions: 1) without doxycycline, without cumate, 2) with doxycycline, with cumate, 3) without doxycycline, with cumate, and 4) with doxycycline, without cumate for each of the low, medium and high cell line injected mice. A total of 48 mice are utilized for monitoring scFv production (4 mice for each test group×4 test conditions×3 scFv copy levels). After subcutaneous injection of cells, mice are given an i.p. bolus of inducer (1 mg doxycycline and/or 150 mg cumate, or vehicle control). Approximately 6 hours after implantation, mice are imaged for the presence of synthetic platform chromosome engineered D1 MSCs producing luciferase utilizing the IVIS (In Vivo Imaging System; PerkinElmer, Inc.) and a tail vein blood draw sample is tested for luciferase activity as described above. Additional samples are collected and tested on days 1, 3, 7, 10 and 14. For each time point, blood samples are taken 6 hours after the days i.p. administration of inducer (or vehicle control).

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of the present invention are embodied by the appended claims. In the claims that follow, unless the term "means" is used, none of the features or elements recited therein should be construed as means-plus-function limitations pursuant to 35 U.S.C. § 112, ¶6.

We claim:

1. An extragenomic mammalian synthetic chromosome able to act as a regulatable portable biological circuit board in the context of a host mammalian cell, comprising:
   a synthetic chromosome tag;
   an active centromeric sequence comprising amplified ribosomal DNA;
   multiple copies of a site-specific recombination site; and
   at least two heterologous genes loaded into at least one recombination site, each heterologous gene under control of a different regulatable expression control system,
   wherein when the synthetic chromosome is present in a mammalian host cell:
   expression of a gene 1 is regulated by a first regulatable expression control system;
   expression of a gene 2 is regulated by a second regulatable expression control system; and
   a gene product 1 of gene 1 regulates, via the second regulatable expression control system, the expression of gene 2, such that the expression of the at least two genes act in concert in a biological circuit.

2. The mammalian synthetic chromosome of claim 1, wherein the gene product 1 of gene 1 regulates transcription of gene 2.

3. The mammalian synthetic chromosome of claim 1, wherein at least one of the first and second regulatable expression control systems is selected from the group consisting of a Tet-On, a Tet-Off, a Lac switch inducible, an ecdysone-inducible, a cumate gene-switch and a tamoxifen-inducible system.

4. An isolated cell carrying the mammalian synthetic chromosome of claim 1.

5. The mammalian synthetic chromosome of claim 2, wherein the gene product 1 of gene 1 activates transcription of gene 2.

6. The mammalian synthetic chromosome of claim 2, wherein the gene product 1 of gene 1 suppresses transcription of gene 2.

7. The autonomous mammalian synthetic chromosome of claim 1, further comprising a gene 3 under control of a third regulatable expression control system wherein, when the mammalian synthetic chromosome is present in a host cell, at least one gene product expressed from the group consisting of gene 1 and gene 2 regulates expression of gene 3 via the third regulatable expression control system.

8. The mammalian synthetic chromosome of claim 7, wherein:

(i) the gene products of both gene 1 and gene 2 are necessary to regulate transcription of gene 3 via the third regulatable expression control system; or (ii) the gene product of either gene 1 or gene 2 regulates transcription of gene 3 via the third regulatable expression control system.

9. An isolated cell carrying the mammalian synthetic chromosome of claim 7.

10. The mammalian synthetic chromosome of claim 7, wherein, when the mammalian synthetic chromosome is present in a host cell, at least two gene products expressed from at least two of genes 1, 2 and 3 regulate expression, via transcriptional or translational control, of an endogenous gene in the host cell.

11. The synthetic chromosome of claim 7, wherein expression of at least one of gene of the group consisting of genes 1, 2 and 3 is controlled by a gene product encoded by an endogenous gene in the host cell.

12. The isolated cell of claim 4, wherein the isolated cell is an immune cell, and the synthetic chromosome carried by the immune cell confers increased immune cell survival and/or enhanced immune cell function.

13. The mammalian synthetic chromosome of claim 1, wherein at least three genes of interest and three gene regulatable expression control systems are inserted into the synthetic chromosome, and a gene product of gene 1 regulates transcription of a third gene, or the gene products of gene 1 and gene 2 regulate transcription of the third gene via a third regulatable expression control system.

* * * * *